(12) United States Patent  (10) Patent No.: US 7,460,911 B2
Cosendai et al.  (45) Date of Patent: Dec. 2, 2008

(54) SYSTEM AND METHOD SUITABLE FOR TREATMENT OF A PATIENT WITH A NEUROLOGICAL DEFICIT BY SEQUENTIALLY STIMULATING NEURAL PATHWAYS USING A SYSTEM OF DISCRETE IMPLANTABLE MEDICAL DEVICES

(75) Inventors: Gregoire Cosendai, Cudrefin (CH); Ytizhak Zilberman, Santa Clarita, CA (US); Doug Kuschner, Santa Clarita, CA (US); Anne Marie Ripley, Los Angeles, CA (US); Ruth Turk, Farnham (GB); Jane Burridge, Salisbury (GB); Scott V. Notley, Southhampton (GB); Ross Davis, Melbourne Beach, FL (US); Morten Hansen, Valencia, CA (US); Lee Jay Mandell, West Hills, CA (US); Joseph H. Schulman, Santa Clarita, CA (US); Robert Dan Dell, Valancia, CA (US); John C. Gord, Venice, CA (US)

(73) Assignee: Alfred E. Mann Foundation for Scientific Research, Santa Clara, CA (US)

( * ) Notice: Subject to any disclaimer, the term of this patent is extended or adjusted under 35 U.S.C. 154(b) by 506 days.

(21) Appl. No.: 11/004,758

(22) Filed: Dec. 3, 2004

(65) Prior Publication Data

US 2005/0137648 A1  Jun. 23, 2005

Related U.S. Application Data

(60) Continuation-in-part of application No. 10/391,424, filed on Mar. 17, 2003, now abandoned, which is a division of application No. 09/677,384, filed on Sep. 30, 2000, now Pat. No. 6,564,807, which is a division of application No. 09/048,827, filed on Mar. 25, 1998, now Pat. No. 6,164,284, which is a continuation-in-part of application No. 09/030,106, filed on Feb. 25, 1998, now Pat. No. 6,185,452.

(60) Provisional application No. 60/039,164, filed on Feb. 26, 1997, provisional application No. 60/042,447, filed on Mar. 27, 1997.

(51) Int. Cl.
*A61N 1/08* (2006.01)

(52) U.S. Cl. ............................ 607/48; 607/60; 128/899
(58) Field of Classification Search ................ 607/1–2, 607/32–33, 36, 39–46, 48–49, 59–62, 72–74, 607/77–78; 128/897–899; 600/587, 595
See application file for complete search history.

(56) References Cited

U.S. PATENT DOCUMENTS 4,986,280 A  1/1991  Marcus et al.

(Continued)

FOREIGN PATENT DOCUMENTS

DE  3932405  4/1991

OTHER PUBLICATIONS

Alfieri, Electrical Treatment of Spasticity, Scand J Rehab Med, 1982, pp. 177-172, vol. 14.

(Continued)

*Primary Examiner*—Carl H Layno
*Assistant Examiner*—Jessica Reidel
(74) *Attorney, Agent, or Firm*—Malcolm J. Romano

(57) ABSTRACT

A system and method that facilitates stimulating neural pathways, e.g., muscles and/or associated nerves, of a patient's body for the purpose of therapeutic medical treatment by rehabilitating weakened muscles and using neuroplasticity to retrain sequential muscle movements and/or to provide the ability to directly deliver functional motor movements. Use of the present invention is of particular value for treating a patient following a stroke. More particularly, such systems are characterized by a plurality of discrete devices, preferably battery powered but may alternatively include RF-powered devices as well or in combination, configured for implanting within a patient's body via injection, each device being configured to affect a parameter, e.g., via nerve and/or muscle stimulation and/or to sense a body parameter, e.g., temperature, $O_2$ content, physical position, electrical potential, etc., that operate under control of a system controller that coordinates the sequential stimulation via wireless commands to the implanted devices.

43 Claims, 18 Drawing Sheets

U.S. PATENT DOCUMENTS

| | | | |
|---|---|---|---|
| 5,010,893 A * | 4/1991 | Sholder | 600/595 |
| 5,167,229 A * | 12/1992 | Peckham et al. | 607/48 |
| 5,193,539 A | 3/1993 | Schulman et al. | |
| 5,193,540 A | 3/1993 | Schulman et al. | |
| 5,324,316 A | 6/1994 | Schulman et al. | |
| 5,330,516 A * | 7/1994 | Nathan | 607/48 |
| 5,358,514 A * | 10/1994 | Schulman et al. | 607/61 |
| 5,562,707 A * | 10/1996 | Prochazka et al. | 607/2 |
| 5,748,845 A * | 5/1998 | Labun et al. | 706/10 |
| 5,769,875 A * | 6/1998 | Peckham et al. | 607/48 |
| 5,814,089 A * | 9/1998 | Stokes et al. | 607/32 |
| 5,831,260 A | 11/1998 | Hansen | |
| 6,164,284 A | 12/2000 | Schulman et al. | |
| 6,393,718 B1 | 5/2002 | Harris et al. | |
| 6,472,991 B1 | 10/2002 | Schulman et al. | |
| 6,750,747 B2 | 6/2004 | Mandell et al. | |
| 6,784,775 B2 | 8/2004 | Mandell et al. | |
| 6,804,558 B2 | 10/2004 | Haller et al. | |
| 2001/0053926 A1 * | 12/2001 | Whitehurst | 607/61 |
| 2002/0161415 A1 * | 10/2002 | Cohen et al. | 607/48 |
| 2002/0198472 A1 | 12/2002 | Kramer | |
| 2003/0078634 A1 | 4/2003 | Schulman et al. | |
| 2003/0139783 A1 * | 7/2003 | Kilgore et al. | 607/49 |
| 2004/0011366 A1 * | 1/2004 | Schulman et al. | 128/899 |
| 2004/0153127 A1 | 8/2004 | Gordon et al. | |
| 2004/0158294 A1 | 8/2004 | Thompson | |
| 2004/0183607 A1 | 9/2004 | Moore | |
| 2004/0225335 A1 | 11/2004 | Whitehurst et al. | |

OTHER PUBLICATIONS

Alon, et al, Improving Selected Hand Functions Using a Noninvasive Neuroprosthesis in Persons With Chronic Stroke, Journal of Stroke and Cerebrovascular Diseases, 2002, pp. 99-106, vol. 11, No. 2.

Alon, et al, A Home-Based, Self-Administered Stimulation Program to Improve Selected Hand Functions of Chronic Stroke, NeuroRehabilitation, 2003, pp. 215-225, vol. 18, Publisher: IOS Press, Published in: Baltimore, MD.

Loeb, Bion Development at AMI: Clinical Technical Progress, Sep. 6, 2004, Publisher: Alfred E. Mann Institute for Biomedical Engineering at the University of So. Calif., Published in: Los Angeles.

Bowman, et al, Positional Feedback and Electrical Stimulation: an Automated Treatment for the Hemiplegic Wrist, Arch Phys Med Rehabil, 1979, pp. 497-502, vol. 60.

Burridge, Poster—A Preliminary Clinical Study Using RF Bion Microstimulators to Facilitate Upper Limb Function in Hemiplegia, 2004, Publisher: University of Southampton, Published in: UK.

Burridge, et al, A Preliminary Clinical Study Using RF Bion Microstimulators to Facilitate Upper Limb Function in Hemiplegia, Sep. 2004, Published in: UK.

Burridge, et al, Clinical and Therapeutic Applications of Neuromuscular Stimulation, Neuromodulation, 2001, pp. 147-154, vol. 4, No. 4.

Burridge, et al, A Randomised Controlled Pilot Study to Investigate the Effect of Neuromuscular Electrical Stimulation on Upper Limb, 7th Annual Conference of the IFESS, 2004, Published in: UK.

Cauraugh, et al, Chronic Motor Dysfunction After Stroke, Stroke, 2000, pp. 1360-1364, vol. 31.

Chae, et al, Neuromuscular Stimulation for Upper Extremity Motor and Functional Recovery in Acute Hemiplegia, American Heart Association, Inc., 1998, pp. 975-998, Published in: Cleveland, Ohio.

Fields, Electromyographically Triggered Electric Muscle Stimulation for Chronic Hemiplegia, Arch Phys Med Rehabil, 1987, pp. 407-414, vol. 68.

Francisco, et al, Electromyogram-Triggered Neuromuscular Stimulation for Improving the Arm Function of Acute Stroke Survivors, Arch Phys Med Rehabil, 1998, pp. 570-575, vol 79.

Alon, Use of Neuromuscular Electrial Stimulation in Neureorehabilitation: A Challenge to All, Journal of Rehabilitation Research and Development, 2003.

Hansen, et al, EMG-Controlled Functional Electrical Stimulation of the Paretic Hand, Scand J Rehab Med, 1979, pp. 189-193, vol. 11.

Hendricks, et al, Functional Electrical Stimulation by Means of the "Ness Handmaster Orthosis" in Chronic Stroke Patients. . . , Clinical Rehabilitation, 2001, pp. 217-220, vol. 15.

Keith, et al, Implantable Functional Neuromuscular Stimulation in The Tetraplegic Hand, The Journal of Hand Surgery, 1989, pp. 524-530, vol. 14A, Published in: Cleveland, Ohio.

Kraft, et al, Techniques to Improve Function of the Arm and Hand in Chronic Hemiplegia, Arch Phys Med Rehabil, 1992, pp. 220-227, vol. 73.

Measurand Inc., S700 Joint Angle Shapesensor, 2004, Publisher: Website, Published in: Canada.

Measurand Inc., S720 Miniature Joint Angle Shapesensor, 2004, Publisher: Website, Published in: Canada.

Merletti, et al, A Control Study of Muscle Force Recovery in Hemiparetic Patients During Treatment With Functional Electrical Stimulation, Scand J Rehab Med, 1978, pp. 147-154, vol. 10.

Ness, Handmaster, 2004, Publisher: Website, Published in: Israel.

Ness, Ness Handmaster—Personal System for Upper Limb Rehabilitation, 2004, Published in: Israel.

Neurocontrol, The Neurocontrol Freehand System, 2004, Published in: Cleveland, Ohio.

Popovic, et al, Restitution of Reaching and Grasping Promoted by Functional Electrical Therapy, Artificial Organs, 2002, pp. 271-275, vol. 36, No. 3, Publisher: Blackwell Publishing, Inc.

Popovic, et al, Surface-Stimulation Technology for Grasping and Walking Neuroprotheses, IFEE Engineering in Medicine and Biology, 2001, pp. 82-93.

Powell, et al, Electrical Stimulation of Wrist Extensors in Poststroke Hemiplegia, Stroke, 1999, pp. 1384-1389, vol. 30, Published in: Scotland.

Sonde, et al, Stimulation With Low Frequency (1.7Hz) Transcutaneous Electric Nerve Stimulation (Low-Tens) Increases Motor Function . . . , Scand J. Rehab Med, 1998, pp. 95-99, vol. 30.

Taylor, et al, Limb Blood Flow, Cardiac Output and Quadriceps Muscle Bulk Following Spinal Cord Injury . . . , Paraplegia, 1993, pp. 303-310, vol. 31, Publisher: International Medical Society of Paraplegia.

Loeb et al, Bion Implants for Therapeutic and Functional Electrical Stimulation, Neural Prostheses for Restoration of Sensory and Motor Function, 2001, pp. 75-99, Publisher: CRC Press, Published in: USA.

Troyk, et al, Development of Bion Technology for Functional Electrical Stimulation: Bidirectional Telemetry, 2001 Proceedings of the 23rd Annual EMBS International Conference, Oct. 25, 2001, pp. 1317-1320, Publisher: IEEE, Published in: Istanbul, Turkey.

Loeb, et al, Bion Implants for Therapeutic and Functional Electrical Stimulation, Neural Prostheses for Restoration of Sensor and Motor Function, 2000, pp. 1-26, Publisher: CRC Press, Published in: Boca Raton, FL.

Loeb, et al, Bion System for Distributed Neural Prosthetic Interfaces, 2001, pp. 1-23, Publisher: Journal of Medical Engineering and Physics, Published in: Los Angeles, CA.

* cited by examiner

OPEN LOOP CONTROL/MONITOR

CLOSED LOOP CONTROL

EXEMPLARY INJURY

COORDINATED CLOSED LOOP HAND CONTROL

SYSTEM AND METHOD SUITABLE FOR TREATMENT OF A PATIENT WITH A NEUROLOGICAL DEFICIT BY SEQUENTIALLY STIMULATING NEURAL PATHWAYS USING A SYSTEM OF DISCRETE IMPLANTABLE MEDICAL DEVICES

This application is a continuation-in-part of U.S. patent application Ser. No. 10/391,424, filed Mar. 17, 2003. U.S. patent application Ser. No. 10/391,424 is a divisional of U.S. patent application Ser. No. 09/677,384, filed Sep. 30, 2000, now U.S. Pat. No. 6,564,807. U.S. Pat. No. 6,564,807 is a divisional of U.S. patent application Ser. No. 09/048,827, filed Mar. 25, 1998, now U.S. Pat. No. 6,164,284. U.S. Pat. No. 6,164,284 is a continuation-in-part of U.S. patent application Ser. No. 09/030,106, filed Feb. 25, 1998, now U.S. Pat. No. 6,185,452, and claims the benefit of U.S. Provisional Application No. 60/042,447, filed Mar. 27, 1997. U.S. Pat. No. 6,185,452 claims the benefit of U.S. Provisional Application No. 60/039,164 filed, Feb. 26, 1997.

FIELD OF THE INVENTION

The present invention is generally directed to systems of discrete implantable medical devices and in particular to such systems that wirelessly communicate with each other for treatment of a patient with a neurological deficit, e.g., as a consequence of a stroke, by sequentially stimulating neural pathways, e.g., muscles or associated nerves, or providing the ability to deliver functional motor movement sequences to the patient.

BACKGROUND OF THE INVENTION

Stroke is the reportedly third leading cause of death in the United States and other developed countries. It is a major source of disability that often leads to hospitalization and long-term care. There are reported to be more than 100,000 new strokes each year in the UK (the incidence in the US is reportedly similar). Over 80% of strokes are as a result of cerebral infarct and of those, 23% die within one year and 65% gain functional independence. Approximately 75% of middle cerebral artery infarcts result in motor deficit, particularly of the upper limb and 24% of patients have residual upper limb motor loss at three months post-stroke. Various longitudinal studies have investigated the long-term outcome following stroke. For example, it is reported that for 30% to 60% of patients, the paretic arm remains without function and that half of all acute stroke patients starting rehabilitation will have a marked impairment of function of one arm of whom only about 14% will regain useful upper limb function.

Following a stroke, almost all patients undergo a period of rehabilitation (Physiotherapy, Occupational Therapy, Speech and Language Therapy) as appropriate. Although there is now overwhelming evidence that patients treated in specialist stroke units have a better outcome than those treated in general hospitals, there is no conclusive evidence that one conventional physical or occupational therapy is more effective than another, and there has been no conclusive evidence to support the effectiveness of conventional therapy in the treatment of upper limb impairment following stroke.

Unlike tetraplegic patients, whose motor impairment is specifically defined by the level and extent of the injury and whose main problem is grasping due to weak finger flexion, stroke patients, because of the nature of the lesion, have a more complex and varied pattern of motor impairment. Firstly, stroke patients are often unable to grip because of weak wrist extensors rather than an inability to activate finger flexors, and it is often spasticity of the flexor muscles that prevents opening of the hand, thus functionally impairing performance. To perform an effective power grip, or even to manipulate objects, requires the wrist to be held in a functional position of slight extension maintained by activity in the wrist extensors, mainly Extensor Carpi Radialis (ECR) and Extensor Carpi Ulnaris (ECU).

Surface Functional Electrical Stimulation (FES) systems have been used to strengthen wrist extensors and some studies have measured improvement both in muscle strength (grip and wrist extension) and hand function. When stimulation is activated voluntarily, usually by the electromyography (EMG) signal from either the target or a remote muscle, improvement in function has been greater. Achieving a functional movement with surface FES however is rarely possible due to the anatomical arrangement of the extensor muscles of the forearm. ECR and ECU lie deep to the finger extensors, so that in practice it is extremely difficult to activate the wrist extensors without also activating the finger extensors; thus preventing the patient from performing a functional grip. Motor re-learning research has demonstrated that achievement and repetition of functional tasks is essential to effect neuroplastic changes, therefore, although surface FES may improve strength, reduce spasticity and increase range of movement, because it is difficult to stimulate a functional movement, it may be less effective in motor-relearning.

Secondly, in addition to weakness of wrist extension, two other common problems seen following stroke are functionally important: (1) the inability to extend the elbow, and (2) the inability to extend the thumb, because of a combination of weakness and spasticity. Weakness of triceps brachii muscle and spasticity of biceps brachii affect elbow movement and weakness of Extensor Pollicis Longus (EPL) muscle and spasticity in the thumb flexors and opponens pollicis affect thumb movement. Like the wrist extensors, EPL is a difficult muscle to activate with surface stimulation as, for most of its length it lies deep to Extensor Pollicis Brevis (EPB). Inability to effectively extend the elbow considerably reduces the work space in which the individual can function, so that even if they have wrist and finger control, function is impaired. Inability to bring the thumb away from the hand restricts the ability to open the hand for grasping.

During the last decade there have been some substantial developments in Functional Electrical Therapy (FET) and Therapeutic Electrical Stimulation (TES) systems and they have been more widely used and evaluated. Multi-channel surface stimulation devices have been reported in the recent literature. Exemplary of such systems is the Ness Handmaster Neuroprosthesis which combines a plastic splint to provide wrist stabilization and housing for the electrodes that stimulate paralyzed muscles in the forearm and the hand muscle groups. The device was originally designed for patients who have no voluntary control of the wrist or hand, such as tetraplegic patients who have a C5/C6 lesion, but more recently it has been often used by stroke patients who have less disability, yet much more complex movement disorders. The system enables both lateral and palmar grips, using pre-set patterns of stimulation to open and close the hand. Stimulation is triggered by the press of a button mounted on the stimulator case and the splint. The system is designed for holding objects such as a fork or pen for prolonged periods, rather than quick or repetitive movements. The Ness Handmaster is commercially available and FDA cleared.

Although Neuro Muscular Electrical Stimulation (NMES) using surface stimulation has been shown to be effective, there are some disadvantages: attaching electrodes to the skin, and positioning them correctly to achieve the desired movement, discomfort from the sensation of stimulation, and skin irritation of which some have been identified by the users. Implanted and percutaneous FES systems have been used in upper limb applications, most notable are the fully implanted 'Freehand' system and the percutaneous system for correction of shoulder subluxation, both developed by Neurocontrol. The Freehand system was shown to be effective in improving hand function in C5/6 tetraplegia, but required extensive invasive surgery with eight epimysial electrodes sutured to the surface of each target muscle and controlled by a receiver/stimulator mounted on the chest wall. It is believed that such systems are unduly difficult to implant due to the required tunnelling of the interconnections between its multiple electrodes and its receiver/stimulator. Additionally, it is believed that such systems are unnecessarily vulnerable to infections (as noted in cardiac pacemakers) that can follow the leads as an infection pathway.

Power signals are transmitted from a coil mounted on the skin over the receiver/stimulator. The subject controls the device through a range of movements of the opposite shoulder, using a skin-surface mounted position detector. Opening and closing of the hand is usually controlled by shoulder retraction and protraction. Strength of grasp is proportional to the degree of movement. A quick elevation or depression of the shoulder activates locking and unlocking of the hand. Two grips are possible: a lateral grasp, where the fingers are first closed and the thumb brought down against the side of the index finger, used for holding small objects such as a pen or fork, and palmar grasp incorporating thumb abduction to hold large objects such as a bottle. The user selects a grasp by pressing a switch, mounted with the shoulder controller. The same switch is also used to turn the system on and off.

The system is intended as a permanent orthosis in subjects who are not expected to experience any natural recovery. Highly significant improvement in hand function has been reported, but the system is limited in its use almost exclusively to C5/6 tetraplegia. It is very expensive and invasive to implant.

SUMMARY OF THE INVENTION

The present invention is directed to systems for stimulating neural pathways, e.g., muscles and/or associated nerves, of a patient's body for the purpose of therapeutic medical treatment by rehabilitating weakened muscles and using neuroplasticity to retrain sequential muscle movements and/or to provide the ability to directly deliver functional motor movements. Use of the present invention is of particular value for treating a patient following a stroke. More particularly, such systems are characterized by a plurality of discrete devices, RF or battery powered, configured for implanting within a patient's body via injection, each device being configured to affect a parameter, e.g., via nerve and/or muscle stimulation (a neural pathway) and/or to sense a body parameter, e.g., temperature, $O_2$ content, physical position, electrical potential, etc., that operate under control of a system controller that coordinates the sequential stimulation.

In an exemplary environment, a system control unit (SCU) comprises a programmable unit capable of (1) transmitting commands to at least some of a plurality of implanted devices and (2) receiving data signals from at least some of those implanted devices. Preferably, the system operates in a closed loop fashion whereby the commands transmitted by the SCU are dependent, in part, on the content of the data signals received by the SCU.

Implanted devices in this exemplary environment may be configured similarly to the devices described in the commonly owned U.S. Pat. No. 6,164,284 (hereinafter referred to as the '284 patent), incorporated herein by reference in its entirety, and are typically contained within a sealed housing suitable for injection into the patient's body. Each housing preferably contains a power source having a capacity of at least 1 microwatt-hour and power consuming circuitry preferably including a data signal transmitter and receiver and sensor/stimulator circuitry for driving an input/output transducer. Wireless communication between the SCU and the other implanted devices can be implemented in various ways, e.g., via a modulated sound signal, an AC magnetic field, an RF signal, a propagated electromagnetic wave, a light signal, or electrical conduction. Furthermore, in commonly owned U.S. Pat. No. 6,472,991 entitled "Multichannel Communication Protocol Configured to Extend The Battery Life Of An Implantable Device", incorporated herein by reference in its entirety, a communication protocol is described for an exemplary communication protocol for communicating between a master device (also referred to herein and in the associated patents as a system control unit (SCU)) which may be implanted within or in proximity to a patient that communicates with a plurality of discrete implantable slave devices, suitable for implantation via injection, via a wireless communication channel.

Alternatively, implanted devices in this exemplary environment may be configured similarly to the devices described in the commonly owned U.S. Pat. Nos. 5,193,539 and 5,193,540 (herein referred to as the '539 and '540 patents) each of which is incorporated herein by reference in their entirety. Such devices differ from those devices described in the '284 patent in that they do not contain a battery and instead rely upon an externally-provided AC magnetic field to induce a voltage, e.g., via a coil into an internal capacitor, and thus power its internal electronics only when the external AC magnetic field is present. These devices are also referred to as being RF powered. Systems which comprise the present invention may include either the '284 battery-powered or the '539/'540 RF-powered classes of devices or combinations thereof.

In accordance with the present invention, a preferred system for sequentially activating a plurality of distinct neural pathways in a patient's body, is described wherein the system is comprised of (1) a first set of one or more discrete implantable devices suitable for placement proximate to a first neural pathway for stimulating the first neural pathway, (2) a second set of one or more discrete implantable devices suitable for placement proximate to a second neural pathway for stimulating the second neural pathway, wherein each of the implantable devices is contained within a sealed elongate housing having an axial dimension of less than 60 mm and a lateral dimension of less than 6 mm, e.g., less than 1¾ cubic centimeters, and includes at least two electrodes integral with and on opposing ends of the housing, whereby the housings are suitable for injection into the patient's body and the implantable devices are configured for affecting at least one neural pathway of the patient's body via the electrodes in response to first communication/control circuitry mounted within each housing and responsive to a unique predefined identification address for each of the implantable devices, (3) a system controller having second communication/control circuitry configured for wireless communication with the first communication/control circuitry within each of the implantable devices, and wherein following a first activation sequence of the first neural pathway transmitted from the system controller to the first set of implantable devices, the system controller additionally transmits a temporally displaced second activation sequence to the second set of implantable devices.

In a further aspect of embodiments of the present invention, the first neural pathway may correspond to those muscles used to extend the patient's lower vs. upper arm at the patient's elbow and the second neural pathway corresponds to those muscles which extend the patient's wrist. Furthermore, a third neural pathway may be similarly stimulated to extend the patient's fingers, i.e., to ungrasp the fingers of the patient's hand.

In a still further aspect of the present invention, a position sensor, e.g., an external sensor may be positioned proximate to the patient's elbow or wrist where it communicates with the system controller to allow it to determine when to sequentially stimulate the various neural pathways. Alternatively, one or more of the implantable devices may provide the capability to determine their relative positioning and thus determine the relative positioning of the relevant body portions.

Finally, embodiments of the present invention may include a proximity sensor to determine when a portion of the patient's body, e.g., the patient's hand, is proximate to a goal position, e.g., a container, and this information may be communicated, e.g., wirelessly, to the system controller to initiate an additional neural response, e.g., grasping of the container.

The novel features of the invention are set forth with particularity in the appended claims. The invention will be best understood from the following description when read in conjunction with the accompanying drawings.

DETAILED DESCRIPTION OF THE PREFERRED EMBODIMENTS

Figure 1:
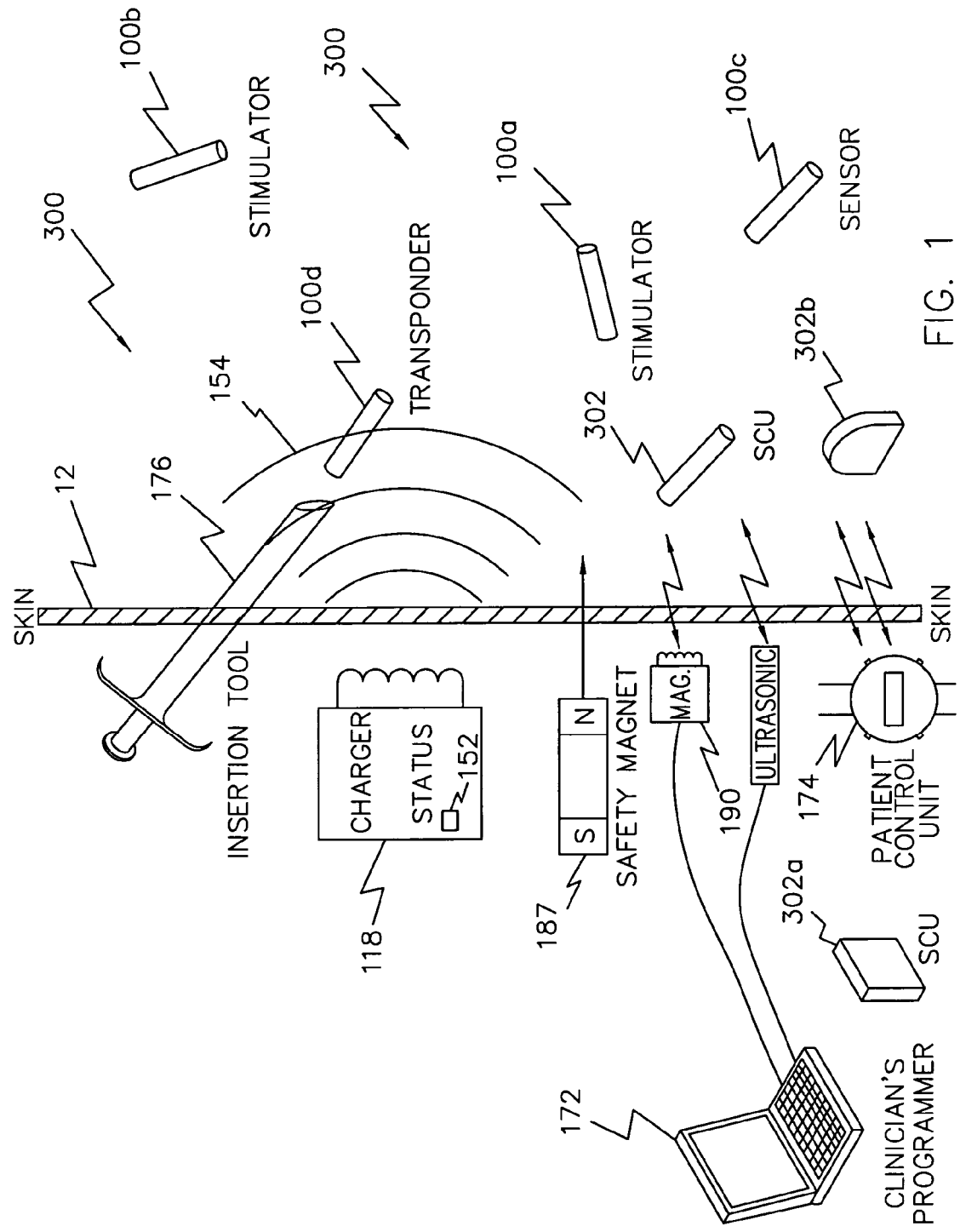
FIG. 1 is a simplified block diagram of an exemplary system suitable for practicing the present invention, the system being comprised of implanted devices, e.g., microstimulators, microsensors and microtransponders, under control of a system control unit (SCU).

The following description is of the best mode presently contemplated for carrying out the invention. This description is not to be taken in a limiting sense, but is made merely for the purpose of describing the general principles of the invention. The scope of the invention should be determined with reference to the claims.

The present invention is directed to systems for stimulating neural pathways, e.g., muscles and/or associated nerves, of a patient's body for the purpose of medical treatment by rehabilitating weakened muscles and using neuroplasticity to retrain sequential muscle movements and/or to provide the ability to directly deliver functional motor movements. Use of the present invention is of particular value for treating a patient following a stroke. More particularly, such systems are characterized by a plurality of discrete devices, preferably battery powered but may include RF-powered devices as well or in combination, configured for implanting within a patient's body via injection, each device being configured to affect a parameter, e.g., via nerve and/or muscle stimulation and/or to sense a body parameter, e.g., temperature, $O_2$ content, physical position, electrical potential, etc., that operate under control of a system controller that coordinates the sequential stimulation.

In an exemplary environment, the SCU (a master device) comprises a programmable unit capable of transmitting commands to at least some of a plurality of implanted devices (slave devices) and may also be capable of receiving data signals from at least some of those implanted devices. Preferably, the system operates, at least in part, in a closed loop fashion whereby the commands transmitted by the SCU are dependent, in part, on the content of the data signals received by the SCU.

Each implanted device in this exemplary environment is configured similarly to the devices described in the commonly owned U.S. Pat. No. 6,164,284 (hereinafter referred to as the '284 patent and incorporated herein by reference in its entirety) and are typically contained within a sealed housing suitable for injection into the patient's body. Each housing preferably contains a power source having a capacity of at least 1 microwatt-hour, preferably a rechargeable battery, and power consuming circuitry preferably including a data signal transmitter and receiver and sensor/stimulator circuitry for driving an input/output transducer.

Alternatively, implanted devices in this exemplary environment may be configured similarly to the devices described in the commonly owned U.S. Pat. Nos. 5,193,539 and 5,193,540, herein referred to as the '539 and '540 patents, each of which is incorporated herein by reference in their entirety. Such devices differ from those devices described in the '284 patent in that they do not contain a battery and instead rely upon an externally-provided AC magnetic field to induce a voltage, e.g., via a coil into an internal capacitor, and thus power its internal electronics only when the external magnetic field is present. These devices are also referred to as being RF powered. Systems which comprise the present invention may include either the '284 battery-powered or '539/'540 RF-powered classes of devices or combinations thereof.

Figure 2:
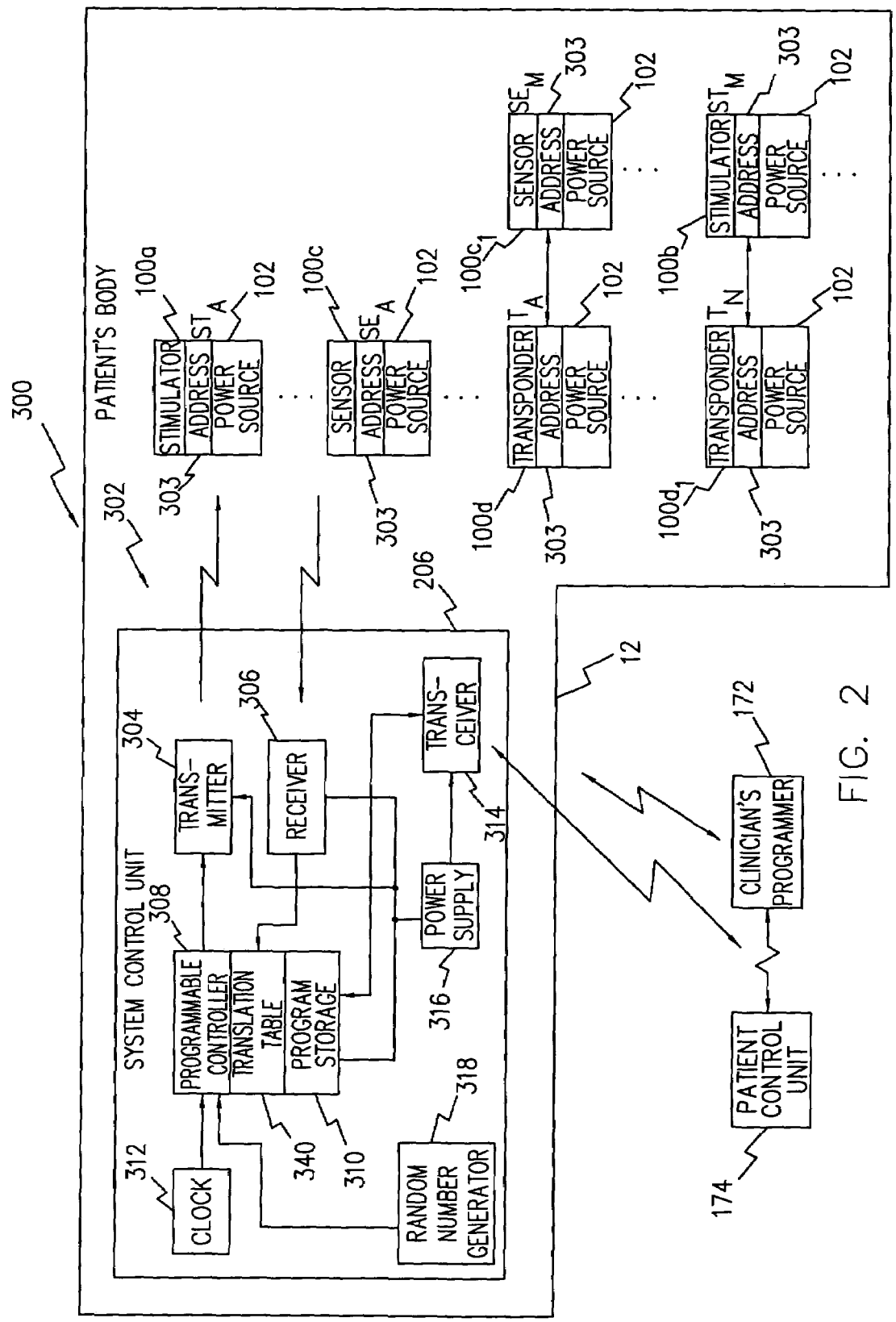
FIG. 2 comprises a block diagram of the system of FIG. 1 showing the functional elements that form the system control unit and implanted microstimulators, microsensors and microtransponders.

FIGS. 1 and 2 show an exemplary system 300 made of implanted devices 100, preferably battery powered, under control of a system control unit (SCU) 302, preferably also implanted beneath a patient's skin 12. As described in the '284 patent, potential implanted devices 100 (see also the block diagram shown in FIG. 3A) include stimulators, e.g., 100a and 100b, sensors, e.g., 100c, and transponders, e.g., 100d. The stimulators, e.g., 100a, can be remotely programmed to output a sequence of drive pulses to body tissue proximate to its implanted location via attached electrodes. The sensors, e.g., 100c, can be remotely programmed to sense one or more physiological or biological parameters in the implanted environment of the device, e.g., temperature, glucose level, $O_2$ content, nerve potential, muscle potential, etc. Transponders, e.g., 100d, are devices which can be used to extend the interbody communication range between stimulators and sensors and other devices, e.g., a clinician's programmer 172 and the patient control unit 174. Preferably, these stimulators, sensors and transponders are contained in sealed elongate housings having an axial dimension of less than 60 mm and a lateral dimension of less than 6 mm. Accordingly, such stimulators, sensors and transponders are respectively referred to as microstimulators, microsensors, and microtransponders or referred to in general as battery-powered, implantable stimulator/sensor devices. Such microstimulators and microsensors can thus be positioned beneath the skin 12 within a patient's body using a hypodermic type insertion tool 176.

As described in the '284 patent, microstimulators and microsensors are remotely programmed and interrogated via a wireless communication channel, e.g., modulated AC magnetic, sound (i.e., ultrasonic), RF or electric fields, typically originating from control devices external to the patient's body, e.g., the clinician's programmer 172 or patient control unit 174. Typically, the clinician's programmer 172 is used to program a single continuous or one time pulse sequence into each microstimulator and/or measure a biological parameter from one or more microsensors. Similarly, the patient control unit 174 typically communicates with the implanted devices 100, e.g., microsensors 100c, to monitor biological parameters. In order to distinguish each implanted device over the communication channel, each implanted device is manufactured with a unique address or identification code (ID) 303 specified in address storage circuitry 108 (see FIG. 3A) as described in the '284 patent. Unique is a relative term, e.g., the more bits used to specify the identification code the easier it will be to distinguish one device or, in the case of master devices, one system of devices from another system of devices. Accordingly, as used in this patent application, unique is only intended to specify that the ID 303 is distinguishable from the IDs of other devices that may exist within the same environment.

By using one or more such implantable devices in conjunction with the SCU 302, the capabilities of such implanted devices can be further expanded. For example, in an open loop mode (described below in reference to FIG. 4), the SCU 302 can be programmed to periodically initiate tasks, e.g., perform real time tasking, such as transmitting commands to microstimulators according to a prescribed treatment regimen or periodically monitor biological parameters to determine a patient's status or the effectiveness of a treatment regimen. Alternatively, in a closed loop mode (described below in reference to FIGS. 5-7), the SCU 302 may periodically interrogate one or more microsensors and accordingly adjust the commands transmitted to one or more microstimulators.

FIG. 2 shows an exemplary system 300 comprised of (1) one or more implantable devices 100 operable to sense and/or stimulate a patient's body parameter in accordance with one or more controllable operating parameters and (2) the SCU 302. The SCU 302 is primarily comprised of (1) a housing 206, preferably sealed and configured for implantation beneath the skin of the patient's body, e.g., as described in the '284 patent in reference to the implanted devices 100, (2) a signal transmitter 304 in the housing 206 for transmitting command signals, (3) a signal receiver 306 in the housing 206 for receiving status signals, and (4) a programmable controller 308, e.g., a microcontroller or state machine, in the housing 206 responsive to received status signals for producing command signals for transmission by the signal transmitter 304 to other implantable devices 100. The sequence of operations of the programmable controller 308 is determined by an instruction list, i.e., a program, stored in program storage 310, coupled to the programmable controller 308. While the program storage 310 can be a nonvolatile memory device, e.g., ROM, manufactured with a program corresponding to a prescribed treatment regimen, it is preferable that at least a portion of the program storage 310 be an alterable form of memory, e.g., RAM, EEPROM, etc., whose contents can be remotely altered as described further below. However, it is additionally preferable that a portion of the program storage 310 be nonvolatile so that a default program is always present. The rate at which the program contained within the program storage 310 is executed is determined by clock/oscillator 312. Additionally, a real time clock operating in response to clock/oscillator 312 preferably permits tasks to be scheduled at specified times of day.

The signal transmitter 304 and signal receiver 306 preferably communicate with implanted devices 100 using an RF signal, e.g., a propagated electromagnetic wave, modulated by a command data signal. Alternatively, an audio transducer may be used to generate mechanical vibrations having a carrier frequency modulated by a command data signal. In an exemplary embodiment, a carrier frequency of 100 kHz or greater, e.g., 128 KHz, 2 MHz, etc., is used which corresponds to a frequency that freely passes through a typical body's fluids and tissues. However, such sound means that operate at any frequency, e.g., greater than 1 Hz, are also considered to be suitable for a potential communication channel. Alternatively, the signal transmitter 304 and signal receiver 306 can communicate using modulated AC magnetic fields.

The clinician's programmer 172 and/or the patient control unit 174 and/or other external control devices can also communicate with the implanted devices 100, as described in the '284 patent, preferably using a modulated RF or AC magnetic field. Alternatively, such external devices can communicate with the SCU 302 via a transceiver 314 coupled to the programmable controller 308. Since, the signal transmitter 304 and signal receiver 306 may operate using a different communication means, a separate transceiver 314 which operates using an alternative communication means may be used for communicating with external devices. However, a single transmitter 304/receiver 306 can be used in place of transceiver 314 for communicating with the external devices and implanted devices if a common communication channel is used.

Figure 3A:
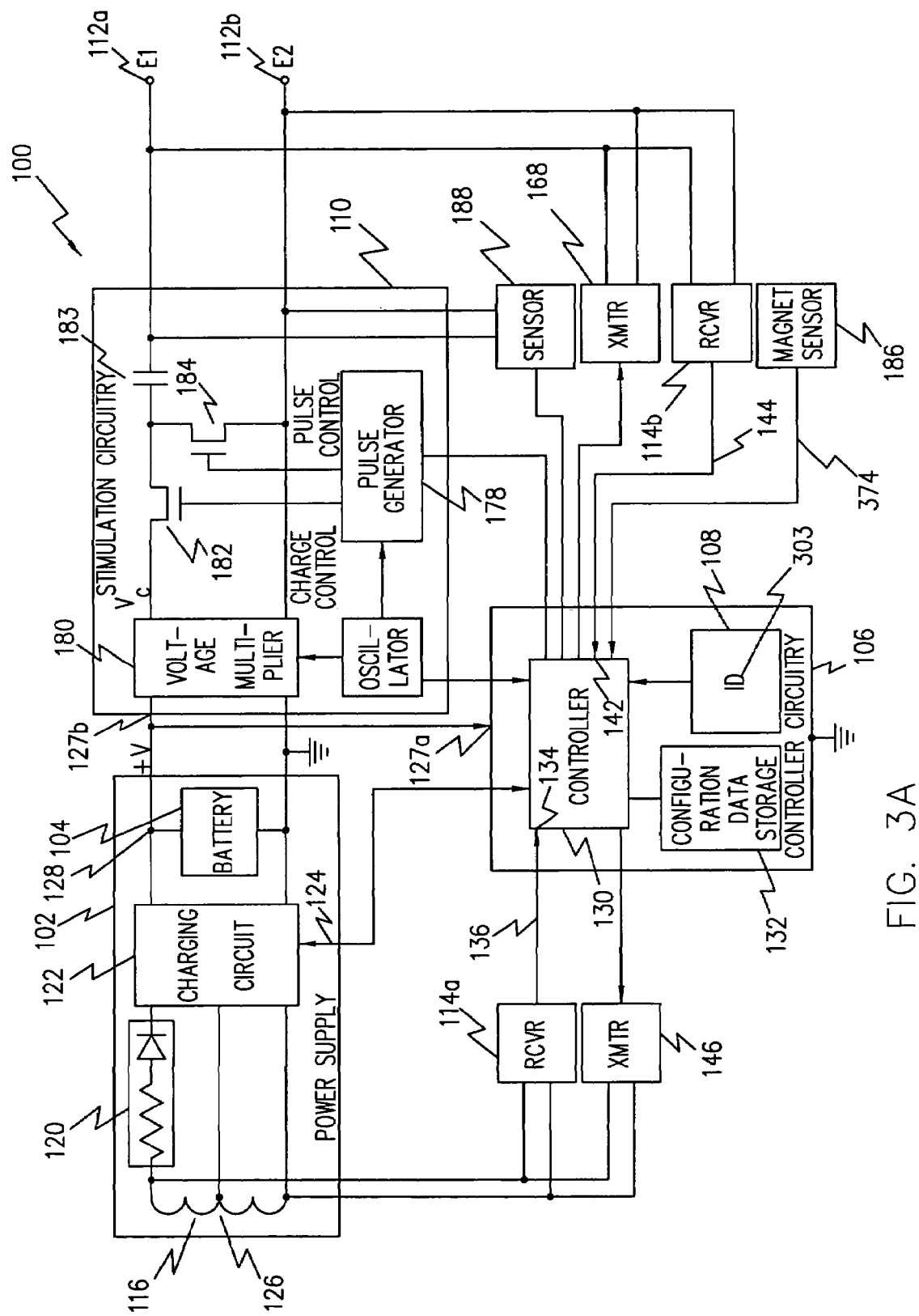
FIG. 3A comprises a block diagram of an exemplary implantable device, as shown in U.S. Pat. No. 6,164,284, including a battery for powering the device for a period of time in excess of one hour in response to a command from the system control unit.
Figure 3B:
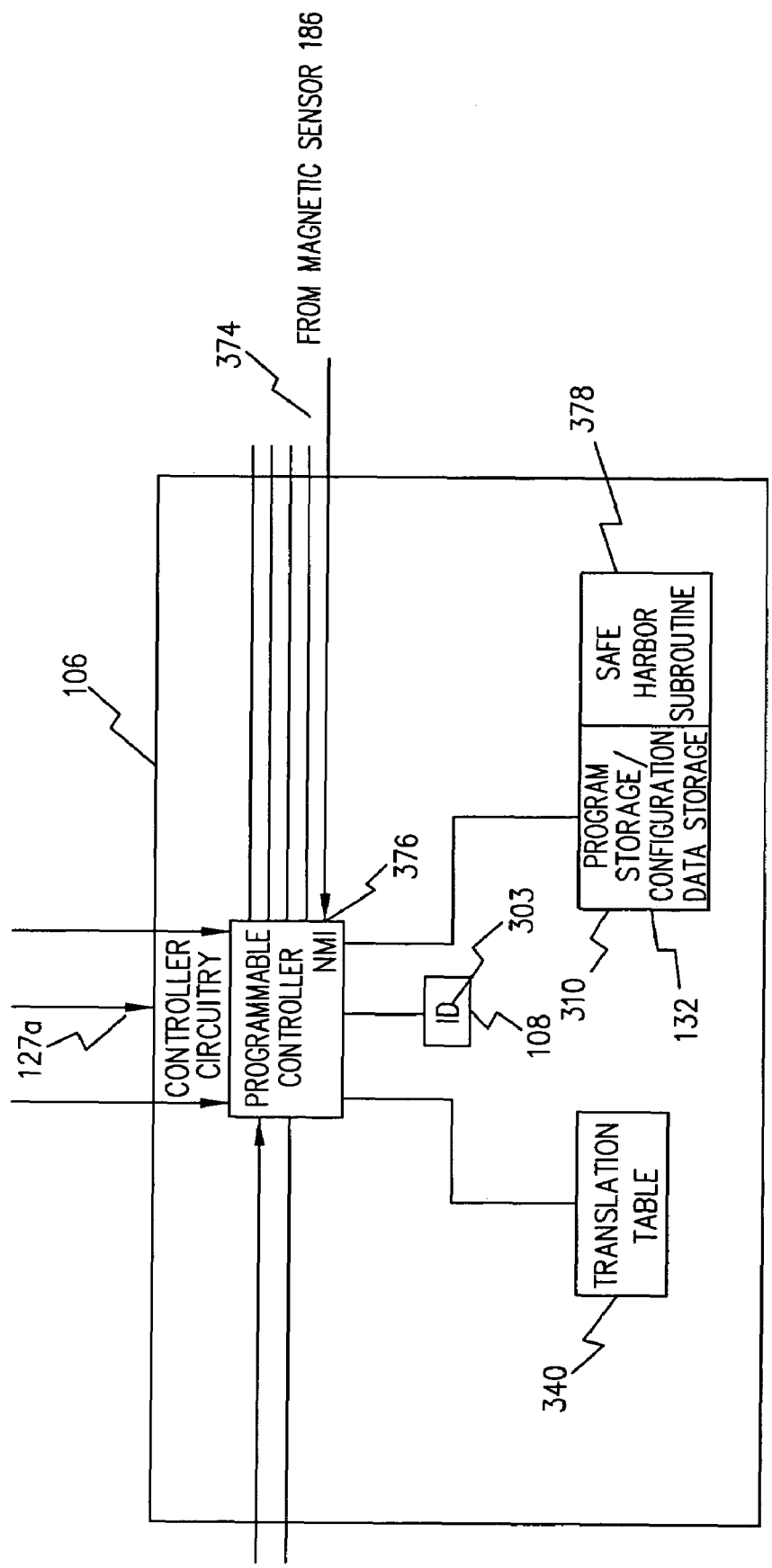
FIG. 3B comprises a simplified block diagram of controller circuitry that can be substituted for the controller circuitry of FIG. 3A, thus permitting a single device to be configured as a system control unit and/or a microstimulator and/or a microsensor and/or a microtransponder.

FIG. 3A comprises a block diagram of an exemplary implantable device 100 operable under control of controller circuitry 106 and includes a battery 104, preferably rechargeable, for powering the device for a period of time in excess of one hour and responsive to command signals from a remote master device, e.g., the SCU 302. The controller circuitry 106 is primarily comprised of a controller 130, configuration data storage 132 for prescribing its operation, and address storage circuitry 108 for storing the ID 303 of the device. As described in the '284 patent, the implantable device 100 is preferably configurable to alternatively operate as a microstimulator and/or microsensor and/or microtransponder due to the commonality of most of the circuitry contained within. Such circuitry may be further expanded to permit a common block of circuitry to also perform the functions required for the SCU 302. Accordingly, FIG. 3B shows an alternative implementation of the controller circuitry 106 of FIG. 3A that is suitable for implementing a microstimulator and/or a microsensor and/or a microtransponder and/or the SCU 302. In this implementation, the configuration data storage 132 can be alternatively used as the program storage 310 when the implantable device 100 is used as the SCU 302. In this implementation, XMTR 168 corresponds to the signal transmitter 304 and the RCVR 114b corresponds to the signal receiver 306 (preferably operable via electrodes 112a and 112b operating as an RF antenna) and the RCVR 114a and XMTR 146 correspond to the transceiver 314 (preferably operable via coil 116 for AC magnetic modes of communication).

Preferably, the contents of the program storage 310, i.e., the software that controls the operation of the programmable controller 308, can be remotely downloaded, e.g., from the clinician's programmer 172 using data modulated onto an RF signal or an AC magnetic field. In this mode, it is preferable that the contents of the program storage 310 for each SCU 302 be protected from an inadvertent change. Accordingly, the contents of the address storage circuitry 108, i.e., the ID 303, is preferably used as a security code to confirm that the new program storage contents are destined for the SCU 302 receiving the data. This feature is particularly significant if multiple patients could be physically located, e.g., in adjoining beds, within the communication range of the clinician's programmer 172.

Preferably, the SCU 302 can operate for an extended period of time, e.g., in excess of one hour, from an internal power supply 316 (see FIG. 2). While a primary battery, i.e., a nonrechargeable battery, is suitable for this function, it is preferable that the power supply 316 include a rechargeable battery, e.g., battery 104 as described in the '284 patent, that can be recharged via an AC magnetic field produced external to the patient's body. Accordingly, power supply 102 of FIG. 3A is the preferred power supply 316 for the SCU 302 as well.

The battery-powered devices 100 of the '284 patent are preferably configurable to operate in a plurality of operational modes, e.g., via a communicated command signal. In a first operational mode, device 100 is remotely configured to be a microstimulator, e.g., 100a and 100b. In this embodiment (see FIG. 3A), controller 130 commands stimulation circuitry 110 to generate a sequence of drive pulses through electrodes 112 to stimulate tissue, e.g., a nerve or muscle, proximate to the implanted location of the microstimulator, e.g., 100a or 100b. In operation, a programmable pulse generator 178 and voltage multiplier 180 are configured with parameters corresponding to a desired pulse sequence and specifying how much to multiply (or divide) the battery voltage (e.g., by summing charged capacitors or similarly charged battery portions) to generate a desired compliance voltage $V_c$. A first FET 182 is periodically energized to store charge into capacitor 183 (in a first direction at a low current flow rate through the body tissue) and a second FET 184 is periodically energized to discharge capacitor 183 in an opposing direction at a higher current flow rate which stimulates a nearby muscle or nerve. Alternatively, electrodes can be selected that will form an equivalent capacitor within the body tissue.

In a next operational mode, the battery-powered implantable device 100 can be configured to operate as a microsensor, e.g., 100c, that can sense one or more physiological or biological parameters in the implanted environment of the device. In accordance with a preferred mode of operation, the system control unit 302 periodically requests the sensed data from each microsensor 100c using its ID 303 stored in the address storage circuitry 108, and responsively sends command signals to microstimulators, e.g., 100a and 100b, adjusted according to the sensed data. For example, sensor circuitry 188 can be coupled to the electrodes 112 to sense or otherwise used to measure a biological parameter, e.g., temperature, glucose level, $O_2$ content, voltage, current, impedance, etc., and provide the sensed data to the controller circuitry 106. Preferably, the sensor circuitry 188 includes a programmable bandpass filter and an analog to digital (A/D) converter that can sense and accordingly convert the voltage levels across the electrodes 112 into a digital quantity. Alternatively, the sensor circuitry 188 can include one or more sense amplifiers to determine if the measured voltage exceeds a threshold voltage value or is within a specified voltage range. Furthermore, the sensor circuitry 188 can be configurable to include integration circuitry to further process the sensed voltage. The operational mode of the voltage sensor circuitry 188 is remotely programmable via the device's communication interface.

Additionally, the sensing capabilities of a microsensor preferably include the capability to monitor the battery status via path 124 from the charging circuit 122 and can additionally include using an ultrasonic transducer, i.e., emitter/receiver (not shown), or the coil 116 to respectively measure the ultrasonic, magnetic or propagated RF signal magnitudes (or communication time delays) of signals transmitted between a pair of implanted devices and thus determine the relative locations of these devices. This information can be used to determine the amount of body movement, e.g., the amount that an elbow or finger is bent, and thus form a portion of a closed loop motion control system. See, for example, commonly assigned U.S. Provisional Patent Application No. 60/497,419, entitled "Goniometry" and its progeny U.S. patent application Ser. No. 10/920,554 which are incorporated herein by reference in their entirety.

In another operational mode, the battery-powered implantable device 100 can be configured to operate as a microtransponder, e.g., 100d. In this operational mode, the microtransponder receives (via the aforementioned RCVR 114a using AC magnetic, sonic, RF, or electric communication modes) a first command signal from the SCU 302 and retransmits this signal (preferably after reformatting) to other implanted devices (e.g., microstimulators, microsensors, and/or microtransponders) using the aforementioned XMTR 168 using magnetic, sonic, RF, or electric communication modes. While a microtransponder may receive one mode of command signal, e.g., magnetic, it may retransmit the signal in another mode, e.g., RF. For example, clinician's programmer 172 may emit a modulated magnetic signal using a magnetic emitter 190 (see FIG. 1) to program/command the implanted devices 100. However, the magnitude of the emitted signal may not be sufficient to be successfully received by all of the implanted devices 100. As such, a microtransponder 100d may receive the modulated magnetic signal and retransmit it (preferably after reformatting) as a modulated ultrasonic or RF signal which can pass through the body with fewer restrictions. In another exemplary use, the patient control unit 174 may need to monitor a microsensor 100c in a patient's foot. Despite the efficiency of ultrasonic, magnetic, and propagated RF communication in a patient's body, such a signal could still be insufficient to pass from a patient's foot to a patient's wrist (the typical location of the patient control unit 174). As such, a microtransponder 100d could be implanted (if needed) in the patient's torso to improve the communication link.

Figure 4:
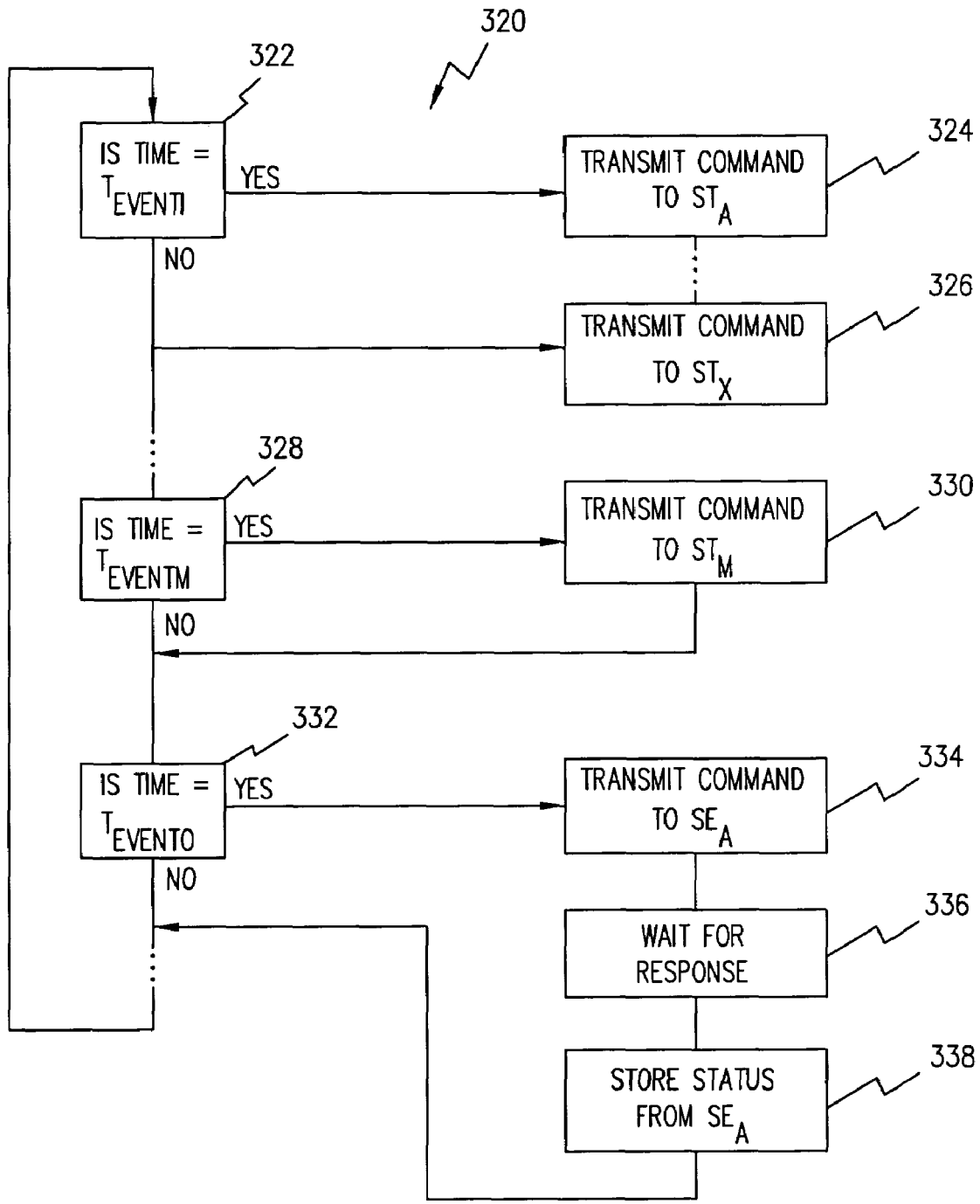
FIG. 4 shows an exemplary flow chart of the use of an exemplary system in an open loop mode for controlling/monitoring a plurality of implanted devices, e.g., microstimulators, microsensors.

FIG. 4 shows a block diagram of an exemplary open loop control program, i.e., a task scheduler 320, for controlling/monitoring a body function/parameter. In this process, the programmable controller 308 is responsive to the clock 312 (preferably a crystal controlled oscillator to thus permit real time scheduling) in determining when to perform any of a plurality of tasks. In this exemplary flow chart, the programmable controller 308 first determines in block 322 if it is now at a time designated as $T_{EVENT1}$ (or at least within a sampling error of that time), e.g., at 1:00 AM. If so, the programmable controller 308 transmits a designated command to microstimulator A ($ST_A$) in block 324. In this example, the control program continues where commands are sent to a plurality of stimulators and concludes in block 326 where a designated command is sent to microstimulator X ($ST_X$). Such a subprocess, e.g., a subroutine, is typically used when multiple portions of body tissue require stimulation, e.g., stimulating a plurality of muscle groups in a paralyzed limb to avoid atrophy. The task scheduler 320 continues through multiple time event detection blocks until in block 328, it determines whether the time $T_{EVENTM}$ has arrived. If so, the process continues at block 330 where, in this case, a single command is sent to microstimulator M ($ST_M$). Similarly, in block 332, the task scheduler 320 determines when it is the scheduled time, i.e., $T_{EVENTO}$, to execute a status request from microsensor A ($SE_A$). If so, a subprocess, e.g., a subroutine, commences at block 334 where a command is sent to microsensor A ($SE_A$) to request sensor data and/or specify sensing criteria. Microsensor A ($SE_A$) does not instantaneously respond. Accordingly, the programmable controller 308 waits for a response in block 336. In block 338, the returned sensor status data from microsensor A ($SE_A$) is stored in a portion of the memory, e.g., a volatile portion of the program storage 310, of the programmable controller 308. The task scheduler 320 can be a programmed sequence, i.e., defined in software stored in the program storage 310, or, alternatively, a predefined function controlled by a table of parameters similarly stored in the program storage 310. A similar process may be used where the SCU 302 periodically interrogates each implantable device 100 to determine its battery status.

Figure 5:
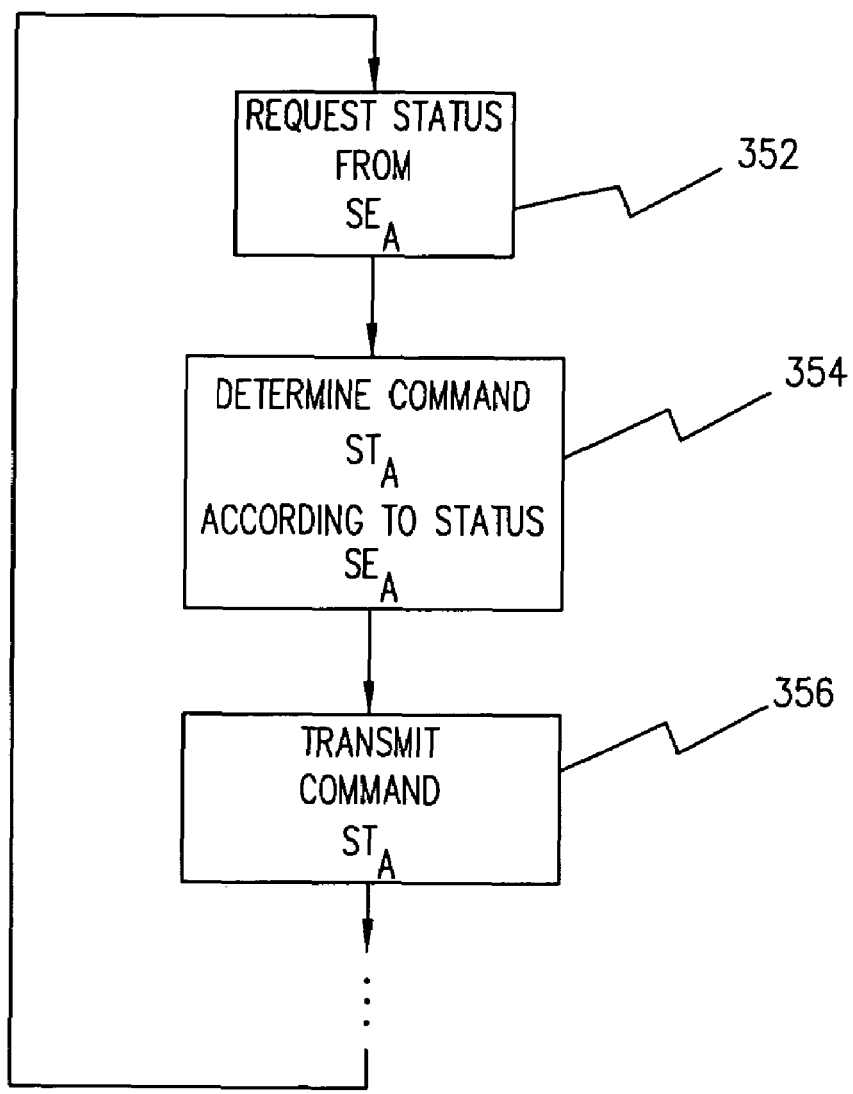
FIG. 5 shows a simplified flow chart of the use of closed loop control of a microstimulator by altering commands from the system control unit in response to status data received from a microsensor.

FIG. 5 is an exemplary block diagram showing the use of such a system to perform closed loop control of a body function. In block 352, the SCU 302 requests status from microsensor A ($SE_A$). The SCU 302, in block 354, then determines whether the present command given to a microstimulator is satisfactory and, if necessary, determines a new command and transmits the new command to the microstimulator A ($ST_A$) in block 356. For example, if microsensor A ($SE_A$) is reading a voltage corresponding to the degree of contraction resulting from stimulating a muscle, the SCU 302 could transmit a command to microstimulator A ($ST_A$) to adjust the sequence of drive pulses, e.g., in magnitude, duty cycle, etc., and accordingly change the voltage sensed by microsensor A ($SE_A$). Accordingly, closed loop, i.e., feedback, control is accomplished. The characteristics of the feedback (proportional, integral, derivative (PID)) control are preferably program controlled by the SCU 302 according to the control program contained in program storage 310.

Figure 6:
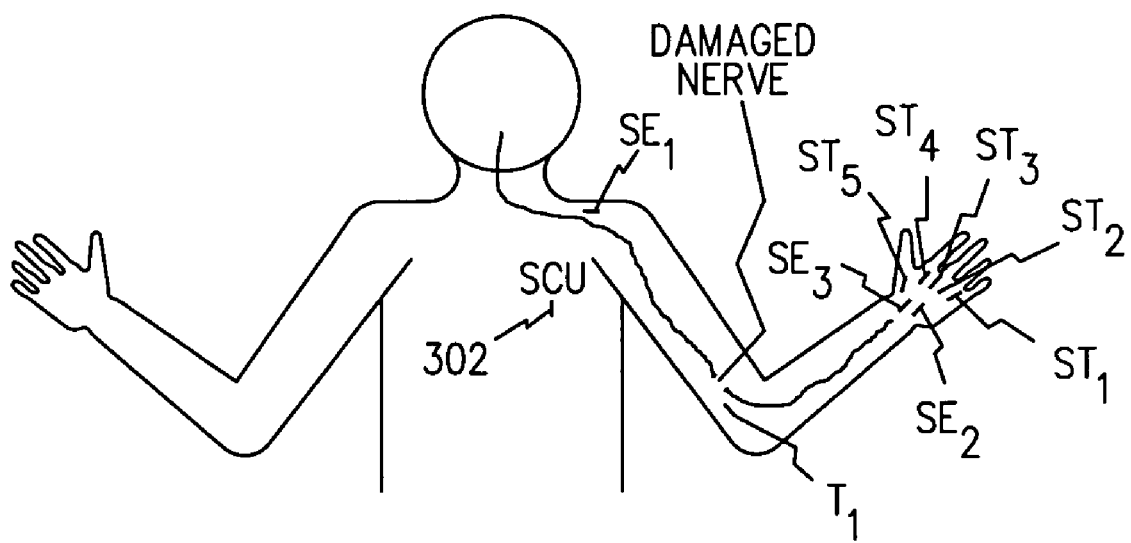
FIG. 6 shows an exemplary injury, i.e., a damaged nerve, and the placement of a plurality of implanted devices, i.e., microstimulators, microsensors and a microtransponder under control of the system control unit for "replacing" the damaged nerve. Similarly, this technology is applicable to treatment following a stroke when neural pathways are damaged within the patient's brain.

FIG. 6 shows an exemplary injury treatable by such an exemplary system 300. In this exemplary injury, the neural pathway has been damaged, e.g., physically or effectively (as a consequence of a stroke or the like) severed, just above the patient's left elbow. The goal of this exemplary system is to bypass the damaged neural pathway to permit the patient to regain control of the left hand. An SCU 302 is implanted within the patient's torso to control a plurality of stimulators, $ST_1$-$ST_5$, implanted proximate to the muscles respectively controlling the patient's thumb and fingers (shown in the patient's hand for simplicity). Additionally, microsensor 1 ($SE_1$) is implanted proximate to an undamaged nerve portion where it can sense a signal generated from the patient's brain when the patient wants hand closure. This technology is equally applicable to use following a stroke where neural pathways within the patient's brain are damaged. Optional microsensor 2 ($SE_2$) is implanted in a portion of the patient's hand where it can sense a signal corresponding to stimulation/motion of the patient's pinky finger and microsensor 3 ($SE_3$) is implanted and configured to measure a signal corresponding to grip pressure generated when the fingers of the patient's hand are closed. Additionally, an optional microtransponder ($T_1$) is shown which can be used to improve the communication between the SCU 302 and the implanted devices.

Figure 7:
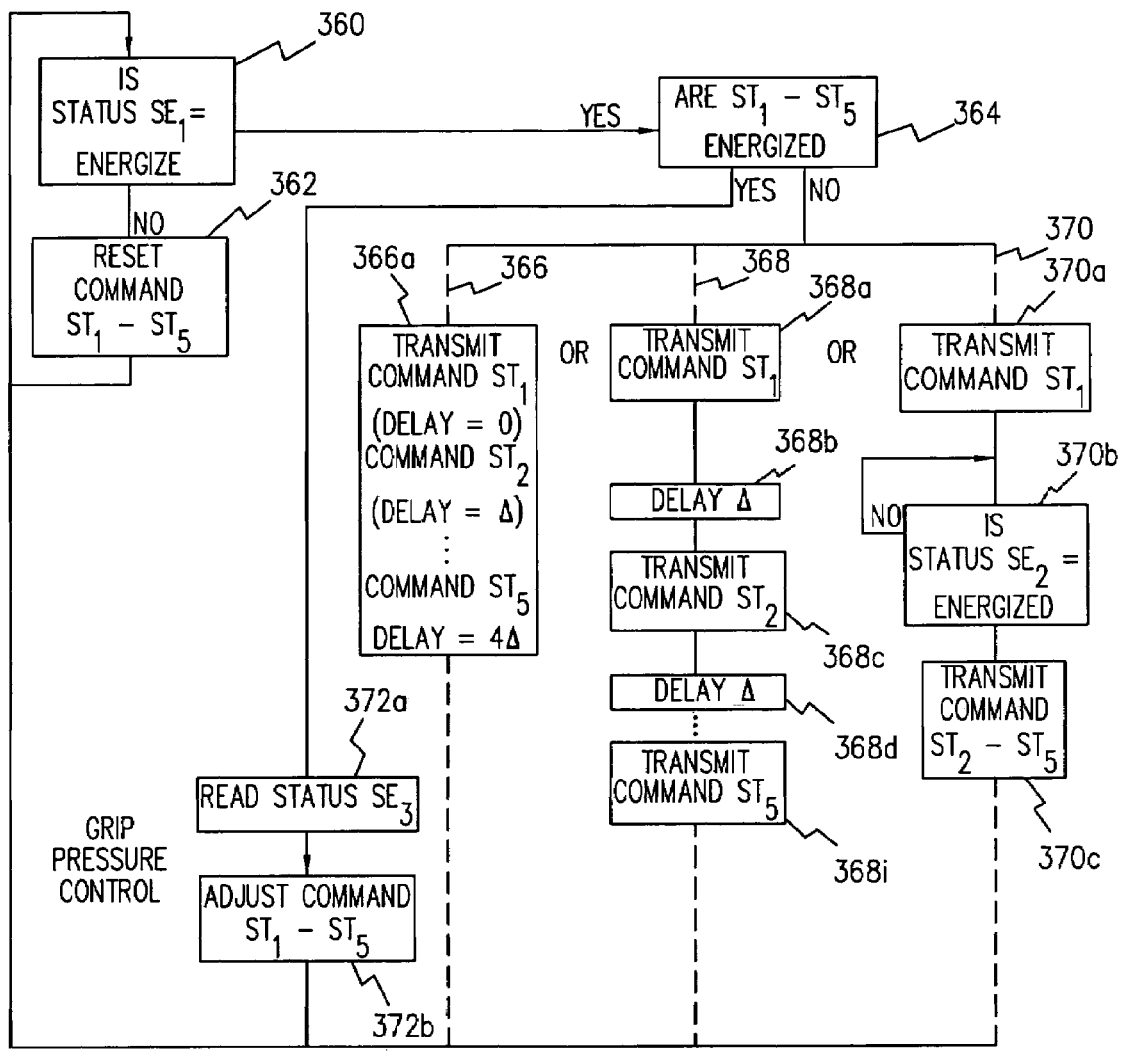
FIG. 7 shows a simplified flow chart of the control of the implanted devices of FIG. 6 by the system control unit.

FIG. 7 shows an exemplary flow chart for the operation of the SCU 302 in association with the implanted devices in the exemplary system of FIG. 6. In block 360, the SCU 302 interrogates microsensor 1 ($SE_1$) to determine if the patient is requesting actuation of his fingers. If not, a command is transmitted in block 362 to all of the stimulators ($ST_1$-$ST_5$) to open the patient's hand, i.e., to de-energize the muscles which close the patient's fingers. If microsensor 1 ($SE_1$) senses a signal to actuate the patient's fingers, the SCU 302 determines in block 364 whether the stimulators $ST_1$-$ST_5$ are currently energized, i.e., generating a sequence of drive/stimulation pulses. If not, the SCU 302 executes instructions to energize the stimulators. In a first optional path 366, each of the stimulators is simultaneously (subject to formatting and transmission delays) commanded to energize in block 366a. However, the command signal given to each one specifies a different start delay time. Accordingly, there is a stagger between the actuation/closing of each finger.

In a second optional path 368, the microstimulators are consecutively energized by a delay $\Delta$. Thus, microstimulator 1 ($ST_1$) is energized in block 368a, a delay is executed within the SCU 302 in block 368b, and so on for all of the microstimulators. Accordingly, paths 366 and 368 perform essentially the same function. However, in path 366 the interdevice timing is performed by the clocks within each implanted device 100 while in path 368, the SCU 302 is responsible for providing the interdevice timing.

In path 370, the SCU 302 actuates a first microstimulator ($ST_1$) in block 370a and waits in block 370b for its corresponding muscle to be actuated, as determined by microsensor 2 ($SE_2$), before actuating the remaining stimulators ($ST_2$-$ST_5$) in block 370c. This implementation could provide more coordinated movements in some situations.

Once the stimulators have been energized, as determined in block 364, closed loop grip pressure control is performed in blocks 372a and 372b by periodically reading the status of microsensor 3 ($SE_3$) and adjusting the commands given to the stimulators ($ST_1$-$ST_5$) accordingly. Consequently, this exemplary system has enabled the patient to regain control of his hand including coordinated motion and grip pressure control of the patient's fingers.

Referring again to FIG. 3A, a magnetic sensor 186 is shown. In the '284 patent, it was shown that such a sensor 186 could be used to disable the operation of an implanted device 100, e.g., to stop or otherwise alter the operation of such devices in an emergency situation, in response to a DC magnetic field, preferably from an externally positioned safety magnet 187 (see FIG. 1). Additionally, it is noted that power to at least some portions of a preferred implantable device may be removed when a magnetic field is sensed and thus power may be conserved. The magnetic sensor 186 can be implemented using various devices. Exemplary of such devices are devices manufactured by Nonvolatile Electronics, Inc. (e.g., their AA, AB, AC, AD, or AG series), Hall effect sensors, magnetoresistive sensors, and subminiature reed switches. Such miniature devices are configurable to be placed within the housing of the SCU 302 and implantable devices 100. While essentially passive magnetic sensors, e.g., reed switches, are possible, the remaining devices may include active circuitry that consumes power during detection of the DC magnetic field. Accordingly, it is preferred that controller 130 periodically, e.g., once a second, provide power to the magnetic sensor 186 and sample the magnetic sensor's output signal 374 during that sampling period. Additionally, a magnetoresistive sensor is especially preferred due to its small size that enables its use within the preferred implantable device 100 while conserving the available internal package volume. Furthermore, as described below, such sensors may be used as a proximity sensor which may be used to provide sequencing information to the system controller, e.g., the SCU 302.

The battery 104 used for powering the implantable device 100 (or SCU 302) is made from appropriate materials so as to preferably provide a power capacity of at least 1 microwatt-hour. Preferably, such a battery, e.g., a Li-I battery, has an energy density of about 240 mw-Hr/$cm^3$. The battery voltage V of an exemplary battery is nominally 3.6 volts, which is more than adequate for operating the CMOS circuits preferably used to implement the IC chip(s) 216, and/or other electronic circuitry, within the SCU 302.

The battery 104 may take many forms, any of which may be used so long as the battery can be made to fit within the small volume available. The battery 104 may be either a primary battery or a rechargeable battery. A primary battery offers the advantage of not requiring a recharging circuit and the disadvantage of not being rechargeable (which means once its energy has been used up, the implanted device no longer functions). Alternatively, as described within this application, RF-powered devices are also applicable to embodiments of the present invention.

A preferred system for practicing the present invention is comprised of an implanted SCU 302 and a plurality of implanted devices 100, each of which contains its own rechargeable battery 104. As such, a patient is essentially independent of any external apparatus between battery chargings (which generally occur no more often than once an hour and preferably no more often than once every 24 hours). However, for some treatment regimens, it may be adequate to use a power supply analogous to that described in U.S. Pat. No. 5,324,316 (herein referred to as the '316 patent and incorporated by reference in Its entirety) that only provides power while an external AC magnetic field is being provided, e.g., from charger 118. Additionally, it may be desired, e.g., from a cost or flexibility standpoint, to implement the SCU 302 as an external device, e.g., within a watch-shaped housing that can be attached to a patient's wrist in a similar manner to the patient control unit 174.

The power consumption of the SCU 302 is primarily dependent upon the circuitry implementation, preferably CMOS, the circuitry complexity and the clock speed. For a simple system, a CMOS implemented state machine will be sufficient to provide the required capabilities of the programmable controller 308. However, for more complex systems, e.g., a system where an SCU 302 controls a large number of implanted devices 100 in a closed loop manner, a microcontroller may be required. As the complexity of such microcontrollers increases (along with its transistor count), so does its power consumption. Accordingly, a larger battery having a capacity of 1 to 10 watt-hours is preferred. While a primary battery is possible, it is preferable that a rechargeable battery be used. Such larger batteries will require a larger volume and accordingly, cannot be placed in the injectable housing described above.

Since only one SCU is required to implement a system, the battery life of the SCU may be accommodated by increasing the casing size (e.g., increasing at least one dimension to be in excess of 1 inch) for the SCU to accommodate a larger sized battery and either locating a larger SCU 302a (see FIG. 1) external to patient's body or a larger SCU 302b may be surgically implanted.

Essentially, there have been described two classes of implantable devices 100, a first which is typically referred to as being RF powered, i.e., it does not contain a battery but instead receives all of its operating power from an externally-provided AC magnetic field (which field is preferably modulated to additionally wirelessly communicate commands to the implantable devices 100), and a second class which is referred to as battery powered which is powered by an internally provided battery which, in turn, is preferably rechargeable and periodically recharged by a similar externally-provided AC magnetic field (see, for example, commonly assigned U.S. Patent Application Publication No. 2003/0078634 corresponding to U.S. patent application Ser. No. 10/272,229, which is incorporated herein by reference in its entirety, which describes recharging environments and techniques for use with such implantable devices) but preferably receives its wireless commands via a modulated RF signal. Thus, in this case, the wireless command signal may be distinct from the wireless charging signal. However, in most other ways, these two classes of implantable devices are similar, e.g., they have similar size restrictions, are suitable for implantation via injection, and can similarly stimulate neural pathways and, thus, they are accordingly generally interchangeable in embodiments of the present invention. Alternatively, embodiments of the present invention may include combinations of RF and battery-powered devices to take advantage of differences, e.g., cost and functional, between both classes of devices.

Figure 8:
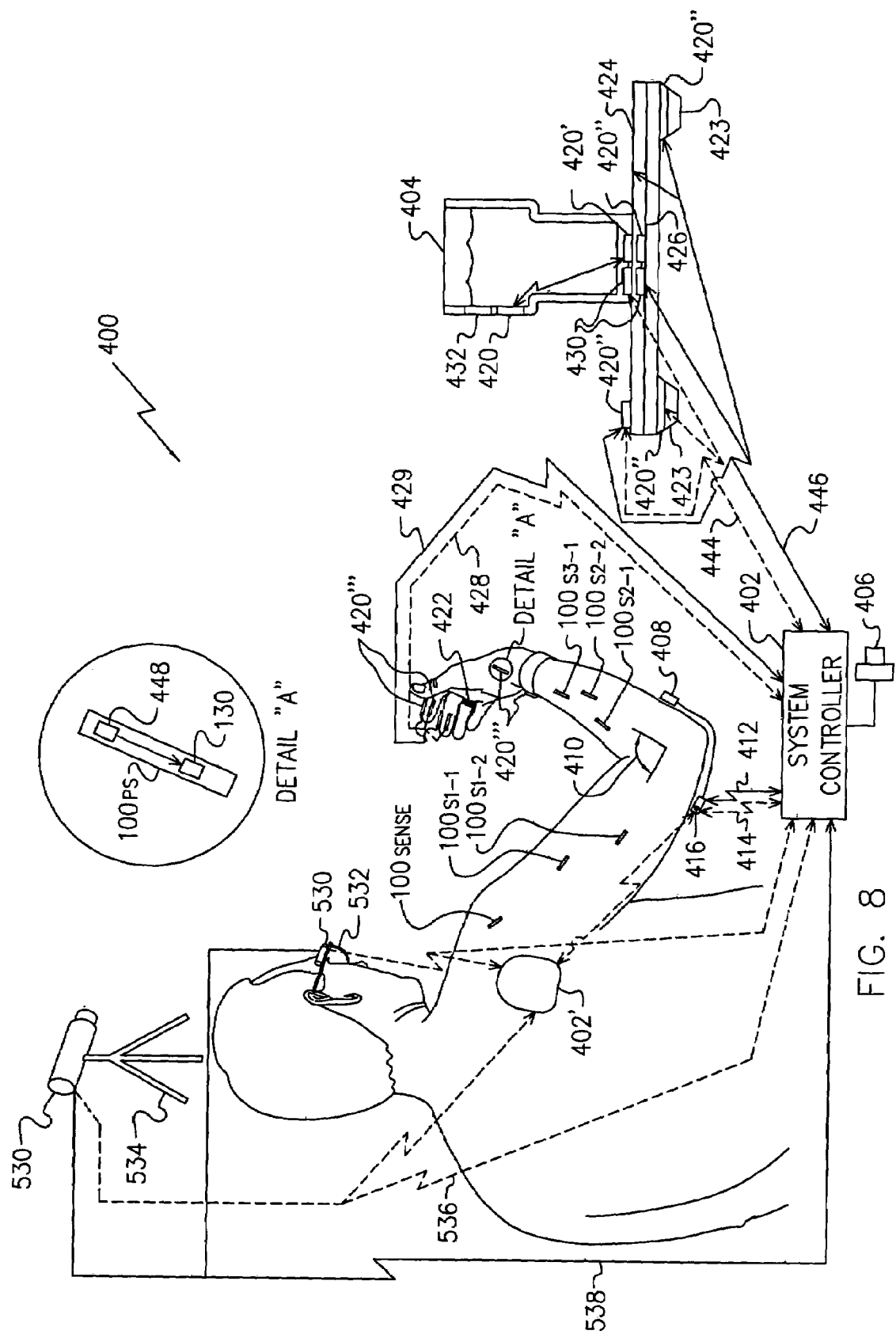
FIG. 8 shows the basic structure of a preferred embodiment of the present invention where a system controller wirelessly communicates with a plurality of sets of implantable devices to achieve therapeutic and/or functional stimulation of muscle groups to compensate for a neurological deficit, e.g., as a result of a stroke.
Figure 9:
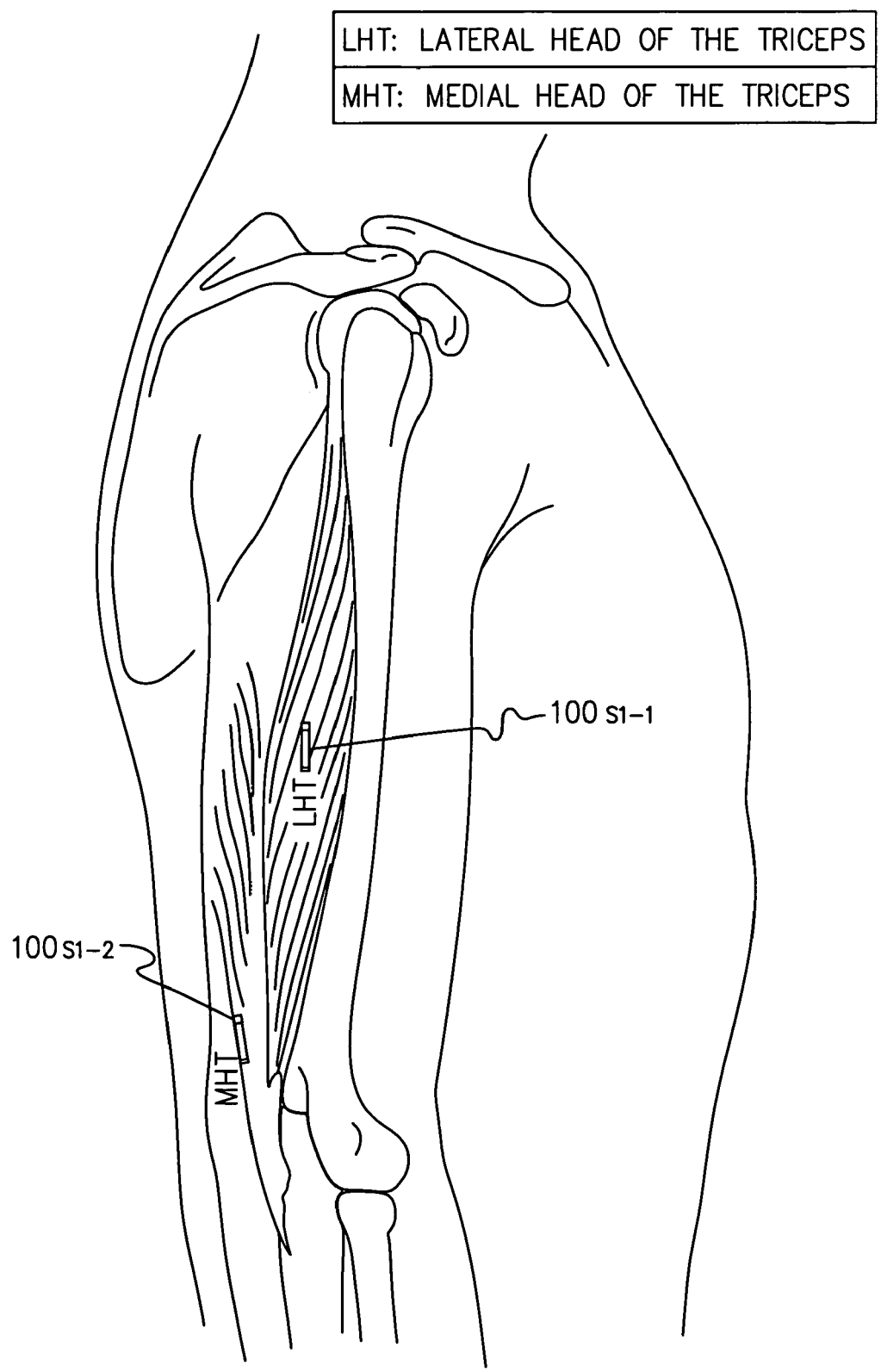
FIG. 9 shows the placement of a first set of implantable devices used for controlling muscle contractions of the patient's upper arm, e.g., via stimulation of the lateral and medial heads of the triceps, and optionally includes the capability to measure movement of the patient's elbow by measuring the degree of contraction of the triceps.
Figure 10:
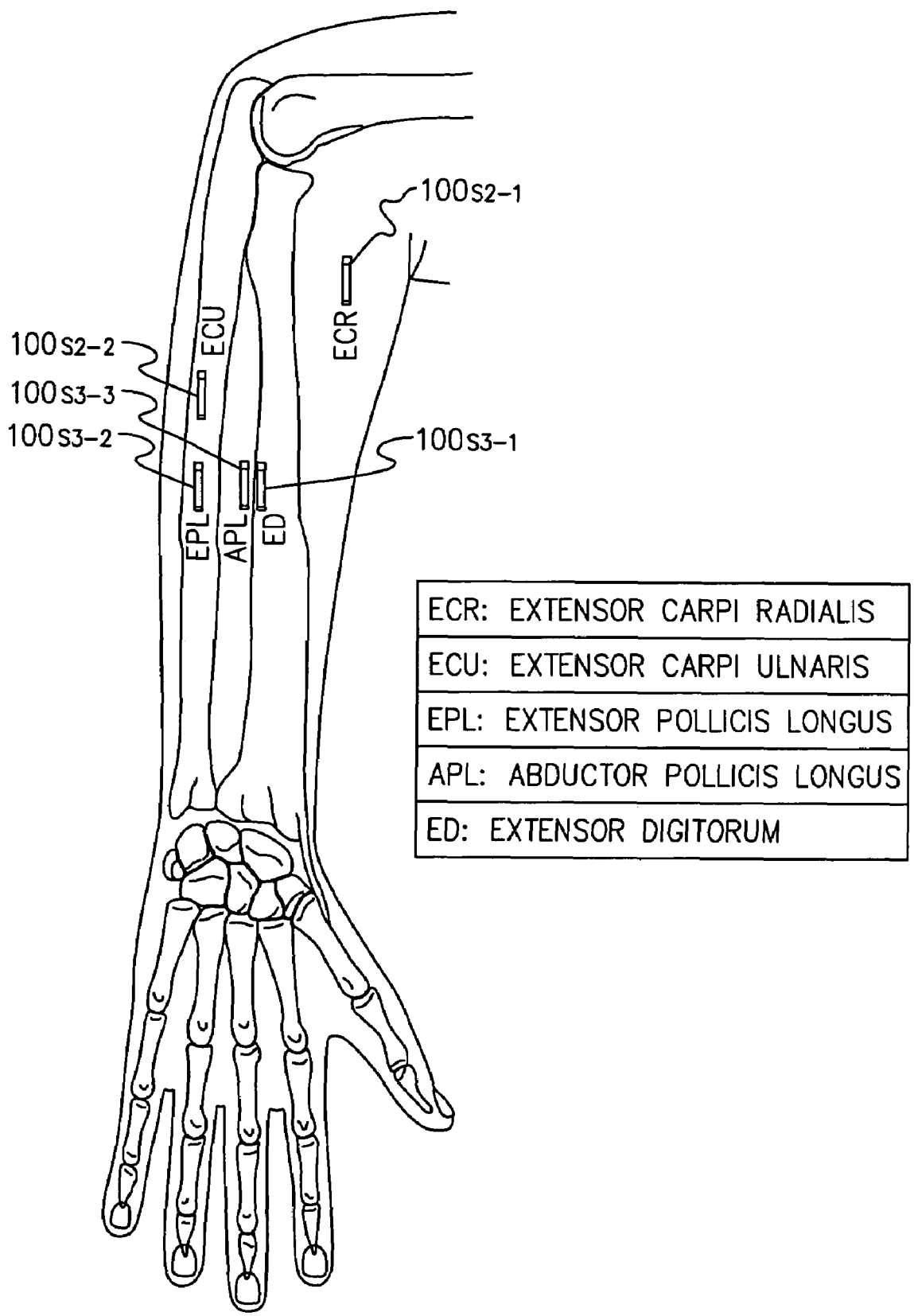
FIG. 10 shows an exemplary placement of a second set of implantable devices used for controlling muscle stimulation to alter the position of the patient's wrist and a third set of implantable devices used for controlling muscle stimulation of the patient's fingers.
Figure 11:
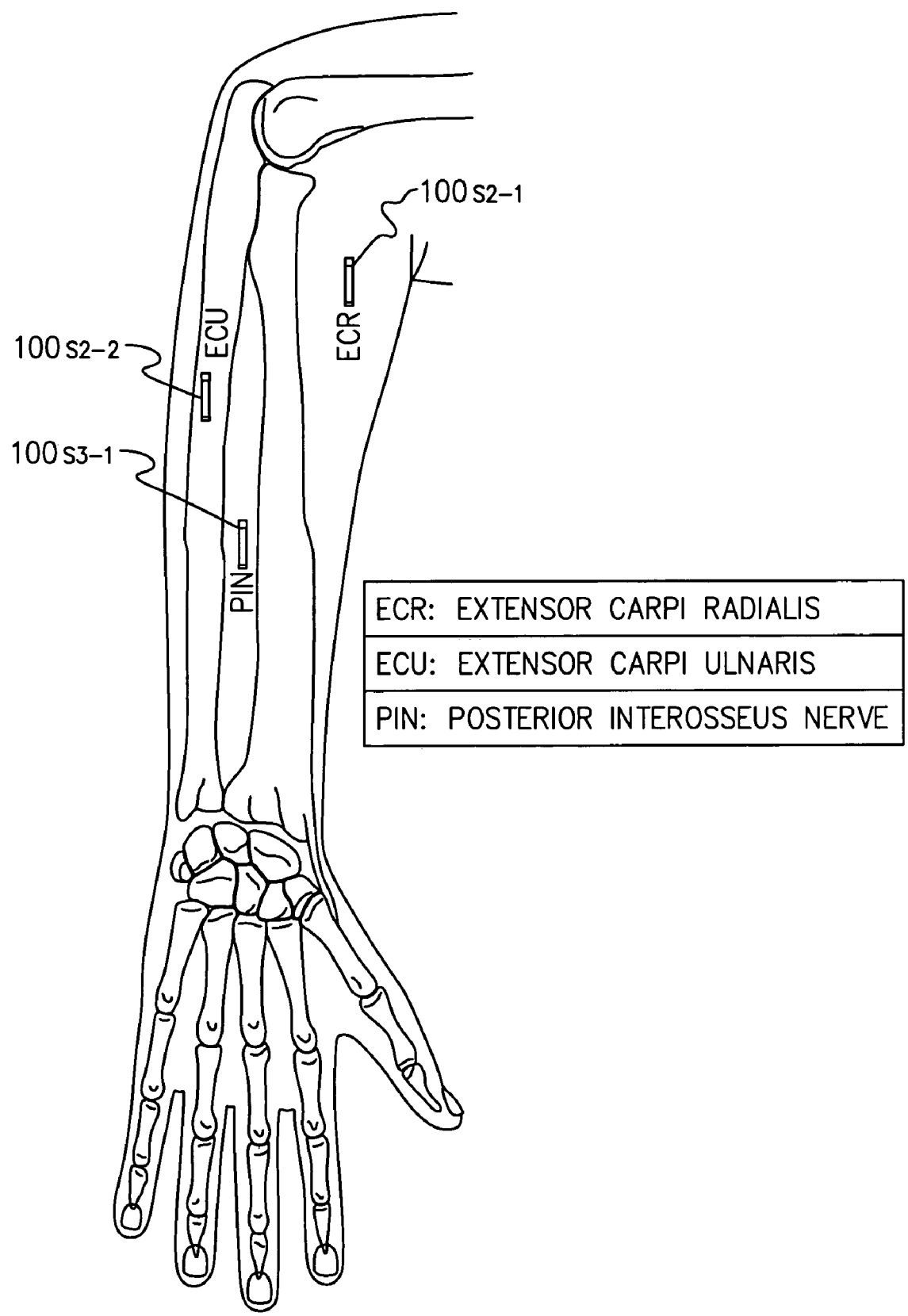
FIG. 11 shows an exemplary placement of a second set of implantable devices used for controlling muscle stimulation to alter the position of the patient's wrist and a third set of implantable devices used for controlling muscle stimulation of the patient's fingers via stimulation of a corresponding nerve.

FIG. 8 shows the basic structure 400 of a preferred embodiment of the present invention. Within this structure 400 are two or more sets of discrete implantable devices, set 1 (e.g., comprised of one or more implantable devices $100_{S1\text{-}1}$, e.g., coupled to the lateral head of the triceps (LHT), $100_{S1\text{-}2}$, e.g., coupled to the medial head of the triceps (MHT)), implanted in a location suitable for stimulating neural pathways (also see FIG. 9), i.e., nerves or muscles, e.g., that are suitable for causing bending of the patient's elbow, set 2 (e.g., comprised of one or more implantable devices $100_{S2\text{-}1}$, e.g., coupled to the Extensor Carpi Radialis (ECR), $100_{S2\text{-}2}$, e.g., coupled to the Extensor Carpi Ulnaris (ECU)), implanted in a location suitable for stimulating neural pathways (also see FIGS. 10 and 11), i.e., nerves or muscles, e.g., that are suitable for causing bending of the patient's wrist, and set 3 (e.g., comprised of one or more implantable devices, e.g., $100_{S3\text{-}1}$, implanted in a location suitable for stimulating neural pathways, i.e., nerves or muscles, e.g., that are suitable for causing bending one or more of the patient's fingers). While the term bending is used throughout this specification, it is intended to include extending and retracting. However, in the currently presented application of the present invention which is used following a stroke, the associated muscles are inherently retracted and the patient has little control over these muscles. Thus, in this particular case, bending is specifically intended to refer to the action of extending the associated body/muscle portions. The choice of whether to use implantable devices to stimulate a nerve or a muscle directly is done by the medical practitioner and each possibility is within the scope of the present invention. For example, in FIG. 11, implantable device $100_{S3\text{-}1}$ is implanted proximate to the Posterior Inerosseus Nerve (PIN) where stimulation of this nerve can stimulate the muscles associated with one or more fingers. Alternatively, in FIG. 10, implantable device $100_{S3\text{-}1}$ is implanted proximate to the Extensor Digitorum (ED) to stimulate the muscles associated with one or more fingers (but not the thumb) and implantable devices $100_{S3\text{-}2}$ and $100_{S3\text{-}3}$ are implanted proximate to the Extensor Pollicis Longus (EPL) and the Abductor Pollicis Longus (APL), respectively extend or bend the patient's thumb. Accordingly, in this alternate embodiment, separate control of the patient's fingers and the patient's thumb can be achieved by separate activations/deactivations of one or more of the implantable devices in the third set.

A system controller 402, e.g., an SCU 302 or the like, is configured to wirelessly communicate with each of these sets of implantable devices 100 and, in response to predetermined timing (or preferably, in response to goniometric feedback), to sequentially activate devices 100 within these sets to cause functional motor movements, e.g., extending of the patient's elbow, extending the patient's wrist, opening the fingers on the patient's hand and then, when the patient's hand is brought into proximity to a destination device 404, e.g., a cup, close the fingers of the patient's hand to retrieve the destination device 404. Optionally, portions of this activation sequence may then be reversed to bring the destination device 404 back towards the patient's body.

The initiation of this sequence may occur in response to various stimuli, e.g., an activation switch 406, or in response to a sensed neurological signal, preferably retrieved from one or more of the implantable devices $100_{SENSE}$ (see, for example, U.S. patent application Ser. Nos. 10/121,881 and 10/920,544 which are incorporated herein by reference in their entirety). Other portions of the sequence occur relative to motor movements, preferably in response to one or more goniometric/distance sensors. In a first embodiment, the goniometric sensor 408 is an external device (see, e.g., the S700 joint angle ShapeSensor™ from Measurand, Inc. of Fredericton, NB Canada) that is attached to or around the patient's elbow to sense elbow motor movement (see the relative angular position 410). Depending upon the implementation of the external goniometric sensor 408, this sensor may be physically wired (see path 412) to the external system controller 402, wirelessly coupled (see path 414) to the external system controller 402 (using an integral communication circuitry 416) or wirelessly communicate with an internal system controller 402', etc. Alternatively, as previously discussed, certain implementations of the implantable devices 100 are capable of performing goniometric measurements internal to the patient's body by sending and receiving signal between two or more of such devices 100 (see, for example, the prior discussion of the use of such devices for goniometry and the commonly assigned U.S. Provisional Patent Application No. 60/497,419, entitled "Goniometry" and its progeny U.S. patent application Ser. No. 10/920,554 which are incorporated herein by reference in their entirety). Such a sensor (formed of two or more implantable devices, e.g., $100_{S1\text{-}2}$ and $100_{S2\text{-}1}$ or $100_{S1\text{-}1}$ and $100_{S1\text{-}2}$) may wirelessly communicate with the external system controller 402, wirelessly communicate with an internal system controller 402', etc. For example, in the first example using devices $100_{S1\text{-}2}$ and $100_{S2\text{-}1}$, communication between these devices allows measurement of the actual movement of the patient's elbow by directly measuring changes in the distance between these devices which corresponds to movement of the patient's elbow. In the second example using devices $100_{S1\text{-}1}$ and $100_{S1\text{-}2}$, changes in the distance between these devices measure the amount of extension or retraction of the patient's triceps.

Figure 12:
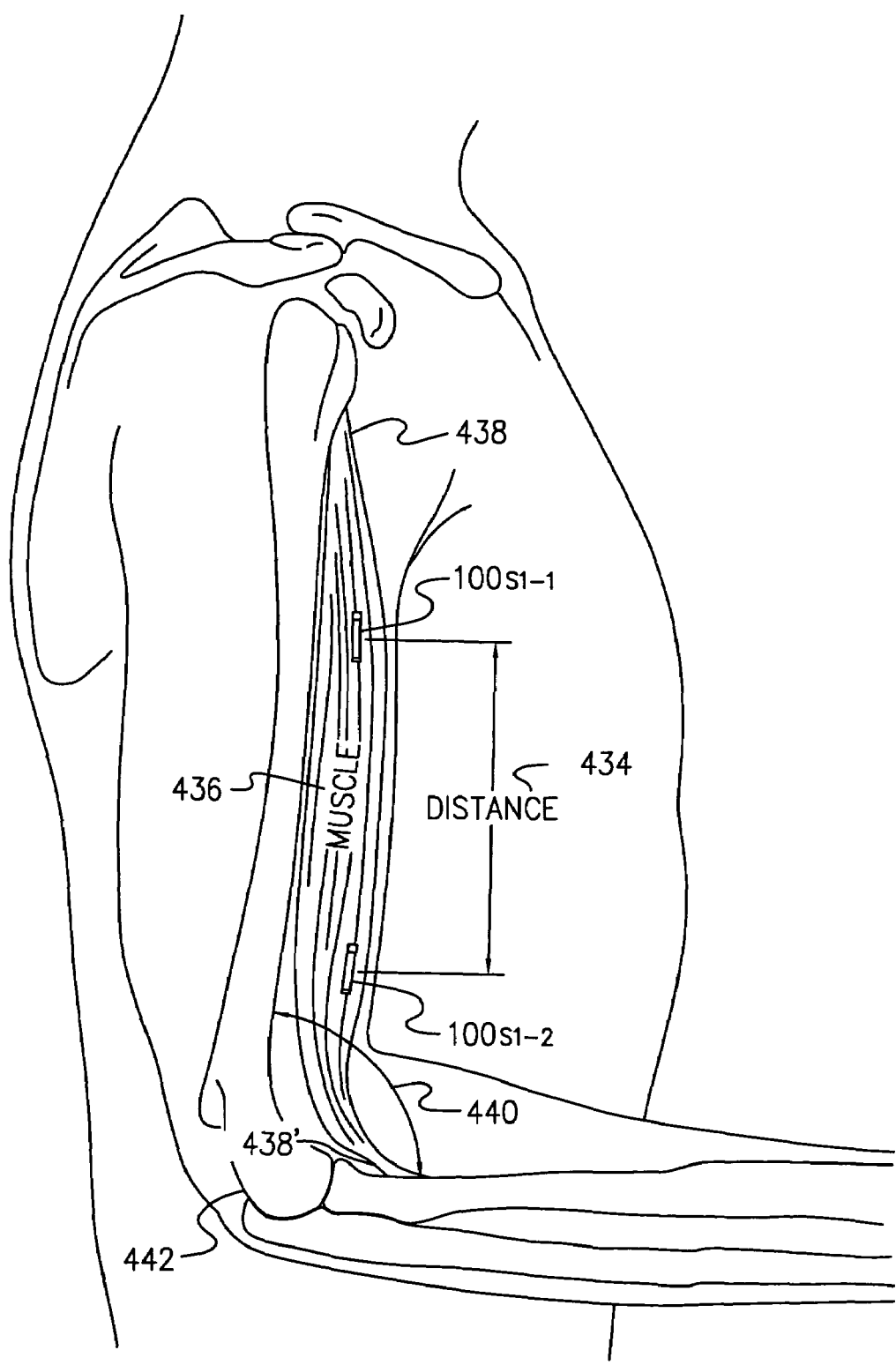
FIG. 12 shows an exemplary placement of two implantable devices that are used to measure the distance between portions of a muscle and consequently corresponds to the joint angle resulting from extension or retraction of the muscle.

It is recognized that this goniometric technique is equally applicable to various muscles, e.g., biceps, triceps, etc., or muscle groups having two or more of such devices implanted within. Since the extension or retraction of the patient's triceps causes elbow movement, this is also a quite effective way of making a goniometric measurement. FIG. 12 shows an exemplary placement of two implantable devices $100_{S1\text{-}1}$ and $100_{S1\text{-}2}$ that are used to measure the distance 434 between portions of a muscle 436 coupled to bones via tendons 438 and 438' at opposing ends of the muscle 436 and consequently corresponds to the joint angle 440 resulting from extension or retraction of the muscle. Advantageously, the angle (relative orientations) between the two implantable devices $100_{S1-1}$ and $100_{S1-2}$ stays relatively constant and since the distance between the implantable devices is relatively smaller than embodiments where the implantable devices surround the joint 442, this approach facilitates an improved measurement accuracy. This approach may also be used for estimating digit flexion/location by implanting devices 100 in digit flexor muscles as well as a reference implantable device 100 in a non-moving location in the patient's forearm.

Such implantable devices 100 may also include stimulation circuitry (previously described) that stimulates the various neural pathways.

Additionally, such implantable devices may wirelessly communicate with other implantable devices 100 such that a system controller, while not being physically present, may still exist by being functionally distributed over a plurality of such implanted devices 100.

Similar goniometric sensors (internal or external) may be used for the other motor movements, e.g., to sense wrist or finger extension (see, for example, the S720 miniature joint angle ShapeSensor™ from Measurand, Inc. of Fredericton, NB Canada). However, it is presently preferred that a fitting system 450 (shown in FIG. 13 and described further below) be used to set stimulation parameters, e.g., the pulse frequency and/or amplitude, for the desired muscle extension.

As a final portion of the desired functional movement, it may be desired for the patient to be able to regain the ability to grasp a desired object. To facilitate this goal, embodiments of the present invention preferably include a proximity sensor 420 (see FIG. 8) to determine when a desired position relative to the desired object 404 has been reached. In a first implementation, the desired destination device 404, e.g., a container or a cup, (or its environment) may include circuitry to determine the proximity of the patient's hand to the container 404. This circuitry may include various types of proximity sensors 420, e.g., a magnetic sensor (see, for example, sensor 186 which is described above) or metallic sensor (see, for example, U.S. Pat. No. 6,750,747, the '747 patent, and U.S. Pat. No. 6,784,775, the '775 patent, both to Mandell et al.) which sense a magnetic or metallic ring 422 on the patient's hand, an infrared sensor (see, for example, U.S. Pat. No. 6,393,718, the '718 patent, to Harris et al.) which senses the infrared energy from the patient's hand, an ultrasonic transducer, i.e., emitter/sensor, that senses distance to the patient's hand, a pressure sensor (see, for example, commonly assigned U.S. Provisional Patent Application No. 60/497,391, the '391 application, entitled "Pressure Sensing" and its progeny U.S. patent application Ser. No. 10/921,750, the '750 application) that senses contact with the patient's hand, etc. The aforementioned '747, '775, and '718 patents as well as the '391 and '750 applications are incorporated herein by reference in their entirety. Alternatively, the container 404 may sit upon a pad 424 that is either sensed via a sensor 420' at the lower surface of the container, e.g., using an integral magnetic or metallic layer 426 in pad 424 (see, for example, the '747 and '775 patents to Mandell et al.) or sensor 420' may sense a pressure disruption when the patient's hand makes contact with the container 404. Conversely, similar circuitry 420" (for example, a pressure sensor via resistors that alter in resistance due to force variances in a Wheatstone bridge or an accelerometer) may be included within, below (e.g., pad feet 423), or on the pad 424 to sense the container 404 or variances in the sensed weight or forces from the container as seen by the pad). In these cases a physical, i.e., non-wireless connection (e.g., path 446) may be made to the external system controller 402. Preferably, this sensing circuitry wirelessly communicates via path 444 using communication circuitry 430 to the system controller 402 (which may be internal or external to the patient's body).

Alternatively, a proximity sensor 420''' (see Detail "A" in FIG. 8) may be included proximate to the patient's hand, i.e., either within or external to, to sense the proximity of the container 404. For example, such sensors 420''' may be attached external to the patient's wrist, implanted within the patient's hand, attached external to one or more of the patient's fingers, implanted within one or more of the patient's fingers, etc. In such a case, the container 404 may contain a magnet or metallic element 432 (which may be the container itself). Alternatively, a pressure sensor, ultrasonic transducer, i.e., emitter/transducer, or accelerometer 448 coupled to the controller 130 (see FIG. 3A), implemented within an implantable device $100_{PS}$ (see Detail "A") implantable in the patient's hand, may detect contact with the container 404. Again, while implanted versions will wirelessly communicate with the system controller 402, e.g., via wireless path 428, and it is preferable that an external proximity sensor 420, 420', or 420" wirelessly communicate as well (see path 444 via communication circuitry 430), an external proximity sensor 420" may alternatively use a hardwired connection (e.g., see paths 446 or 429) to the system controller 402.

Alternatively, paths 412, 429 may include an electrical connection to the patient and path 446 may include an electrical connection to an upper surface of pad 424 that makes electrical contact with the lower surface of the container 404 which is electrically conductive, e.g., metallic, at least on its outer surface. Accordingly, system controller 402 may include circuitry that can detect electrical connection between the patient's hand and the container 404, e.g., by passing a very small current between the patient and the container 404, and thus may detect the patient's hand making contact with the container 404. This circuitry, also referred to in this context as a proximity detector, can use this detected contact to cause the system controller 402 to trigger activation of implantable devices in the third set of implantable devices.

Alternatively, a machine vision based controller may be used for detecting the various phases of the arm movements used in embodiments of the present invention. A machine vision based controller uses a video camera 530 that captures the arm movement, e.g., relative to the destination device 404 and a computer and associated program (either residing at the camera 530, a separate box (not shown), or as a portion of the system controller 402) that operates on the received video and analyzes it using machine vision algorithms to detect such elements as elbow angle and/or proximity (or contact) to the destination device 404. Preferably, this technique does not require the use of special markers on the arm or the destination device 404. The video camera 530 could alternatively be worn by the patient, e.g., as a portion of a pair of eyeglasses 532, or could be mounted on a tripod 534 or other support structure next to the patient. Communication to the system controller may either be wireless via path 536 (system controller 402 or 402') or hardwired via path 538 (system controller 402).

Figure 13:
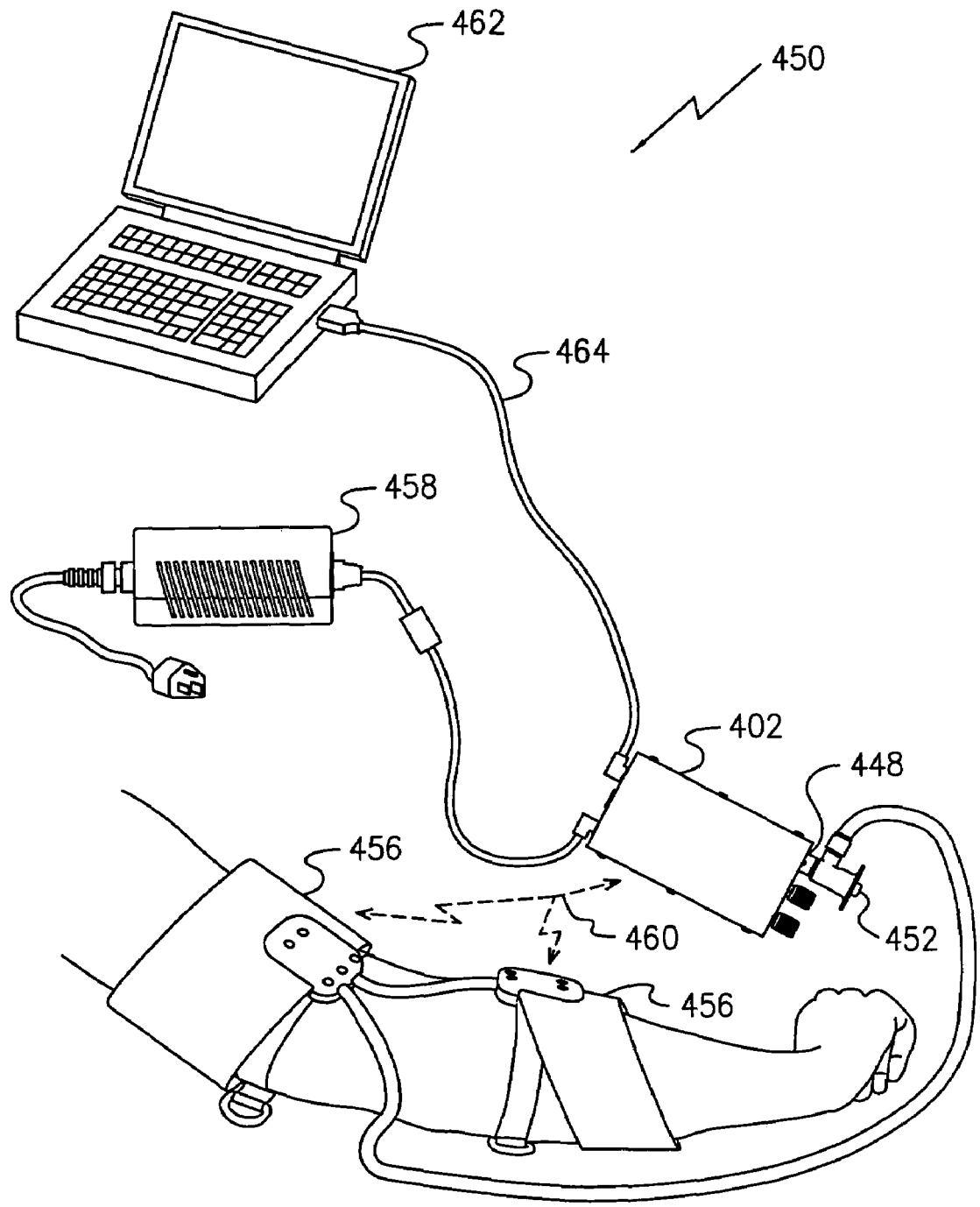
FIG. 13 shows an exemplary structure for fitting, i.e., setting parameters, to the system controller related to an individual patient and charging structures for powering and/or recharging the implantable devices.

FIG. 13 shows an exemplary fitting system 450 that is of particular use with the RF-powered class of implantable devices 100. In this system, the system controller 402 is coupled via connectors 452 and 454 to RF coils 456 that are positioned on the patient's arm proximate to the implanted devices 100 (not shown in this figure). As has been previously described, the RF-powered class of implantable devices derive their power from an AC magnetic field and the AC magnetic field is modulated with data to provided command signals. In this exemplary embodiment, the system controller 402 is preferably powered by a rechargeable battery (not shown) contained within the controller's housing. The rechargeable battery may be recharged via an AC adaptor 458 (or alternatively the AC adaptor 458 may power the system controller 402 directly). In an alternative implementation, the battery-powered class of implantable devices 100 still periodically requires an AC magnetic field to recharge its internal battery. The system of FIG. 13 may be used to provide this charging magnetic field or alternative charging structures may be used (see for example, the charger described in U.S. Patent Application Publication No. 2003/0078634 corresponding to U.S. patent application Ser. No. 10/272,229 which is incorporated herein by reference in its entirety). In this alternative implementation, communication preferably occurs between the system controller 402 and the implantable devices via an RF communication link 460. The parameters, e.g., stimulation parameters, used by the system controller may be adjusted (a process referred to as fitting) via a PC 462 that communicates with the system controller 402 via communication link 464 (which may be wired or wireless). Once the system controller 402 has been programmed and/or its operating parameters have been loaded into the system controller 402, PC 462 may be disconnected and, if the system controller 402 is battery powered, the AC adaptor 458 may be disconnected as well, leaving the system controller 402 as a self sufficient interface to the implantable devices 100.

Figure 14A:
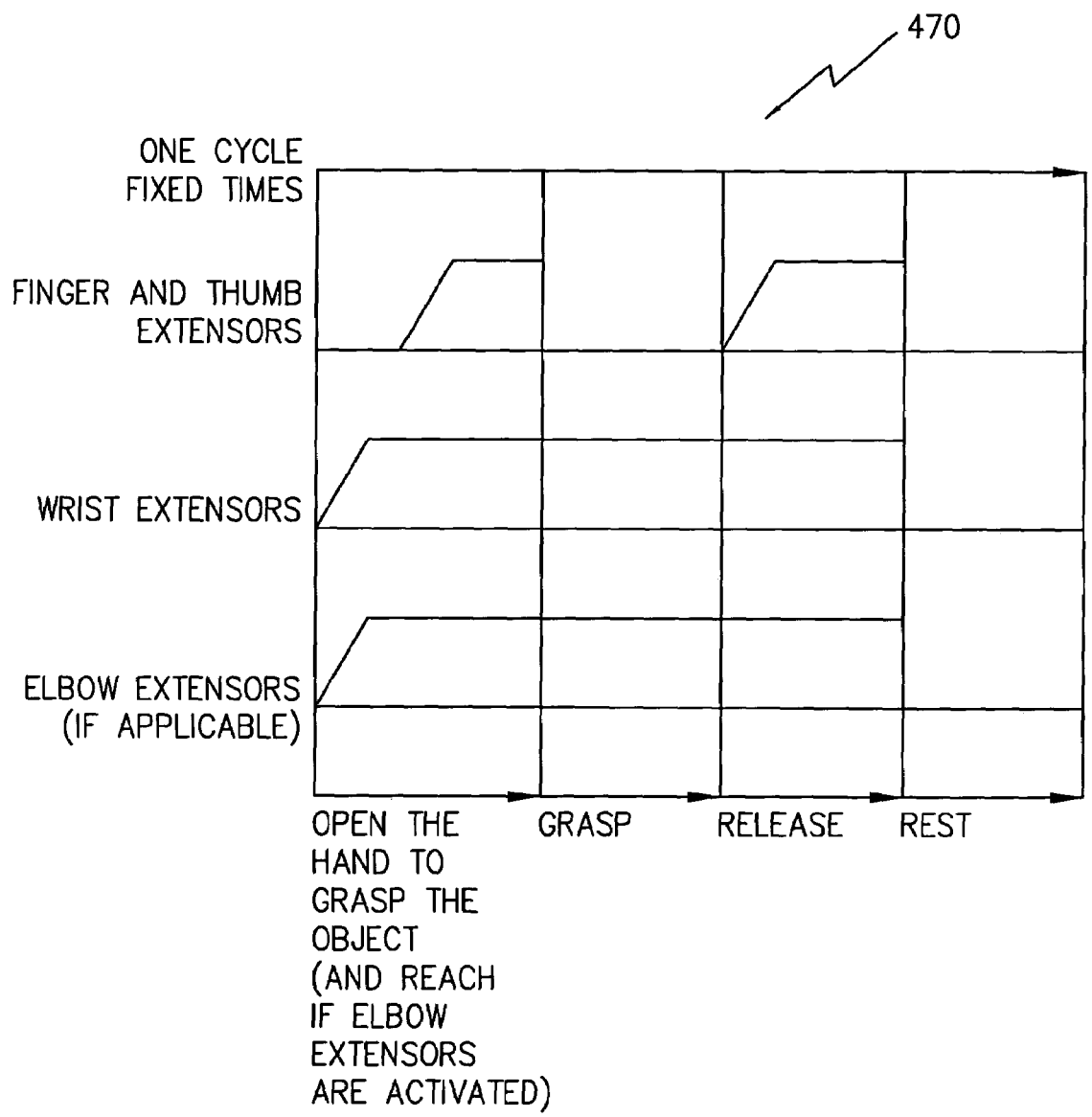
FIGS. 14A and 14B respectively show an exemplary open loop stimulation pattern and associated flow chart for providing a sequence of stimulation signals to muscle groups to provide a therapeutic muscle stimulation sequence to avoid atrophy of the associated muscles and to potentially take advantage of the plasticity of the neural pathways to regain functionality.
Figure 14B:
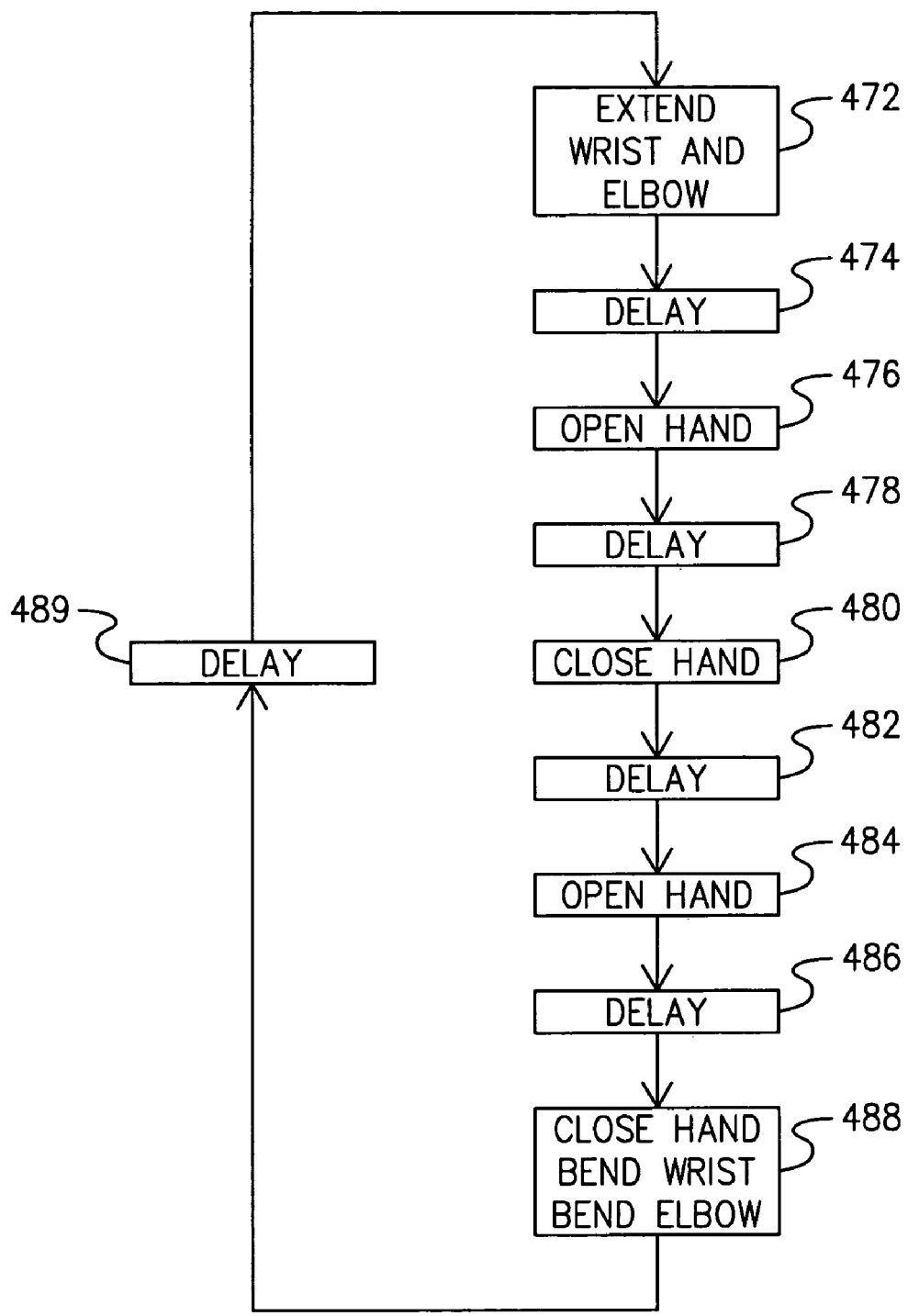

Advantageously, embodiments of the present invention may be used for various purposes, e.g., following a stroke or otherwise caused neural deficit. In a first mode of operation, embodiments of the present invention may be used to strengthen muscles, retrain neural pathways by taking advantage of the neuroplasticity of these pathways, etc. For example, the timing diagram 470 of FIG. 14A and its associated flow chart comprised of blocks 472-489 (see FIG. 14B) that periodically stimulate muscles via associated implantable devices 100 in three sets, a first set for the elbow extensors, a second set for the wrist extensors, and a third set for the finger and thumb extensors. The activation of the associated sets of implantable devices and the timing between activations (or causing concurrent activations) is determined according to a program within the system controller 402 which is preferably user selectable, e.g., via a switch (not shown) on the system controller 402. Preferably, this sequence and associated timing may be determined/altered via the fitting system 450 shown in FIG. 13.

Figure 15A:
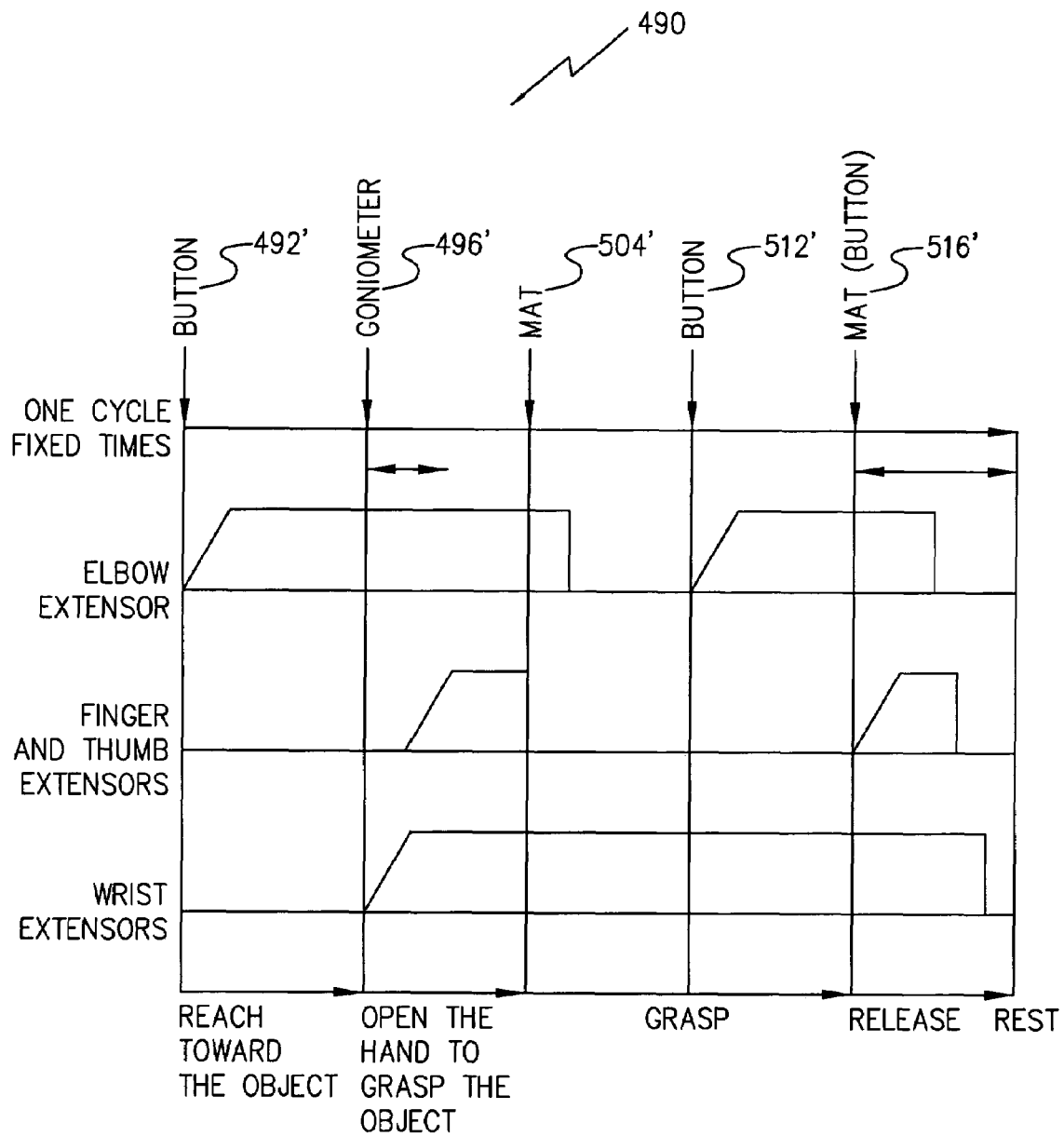
FIGS. 15A and 15B respectively show an exemplary closed loop stimulation pattern and associated flow chart for providing a sequence of stimulation signals to muscle groups to provide a functional muscle stimulation sequence to avoid atrophy of the associated muscles and to potentially take advantage of the plasticity of the neural pathways to regain functionality. In this example, stimulation sequences occur, at least in part, according to sensed movements of body portions in response to these movements.
Figure 15B:
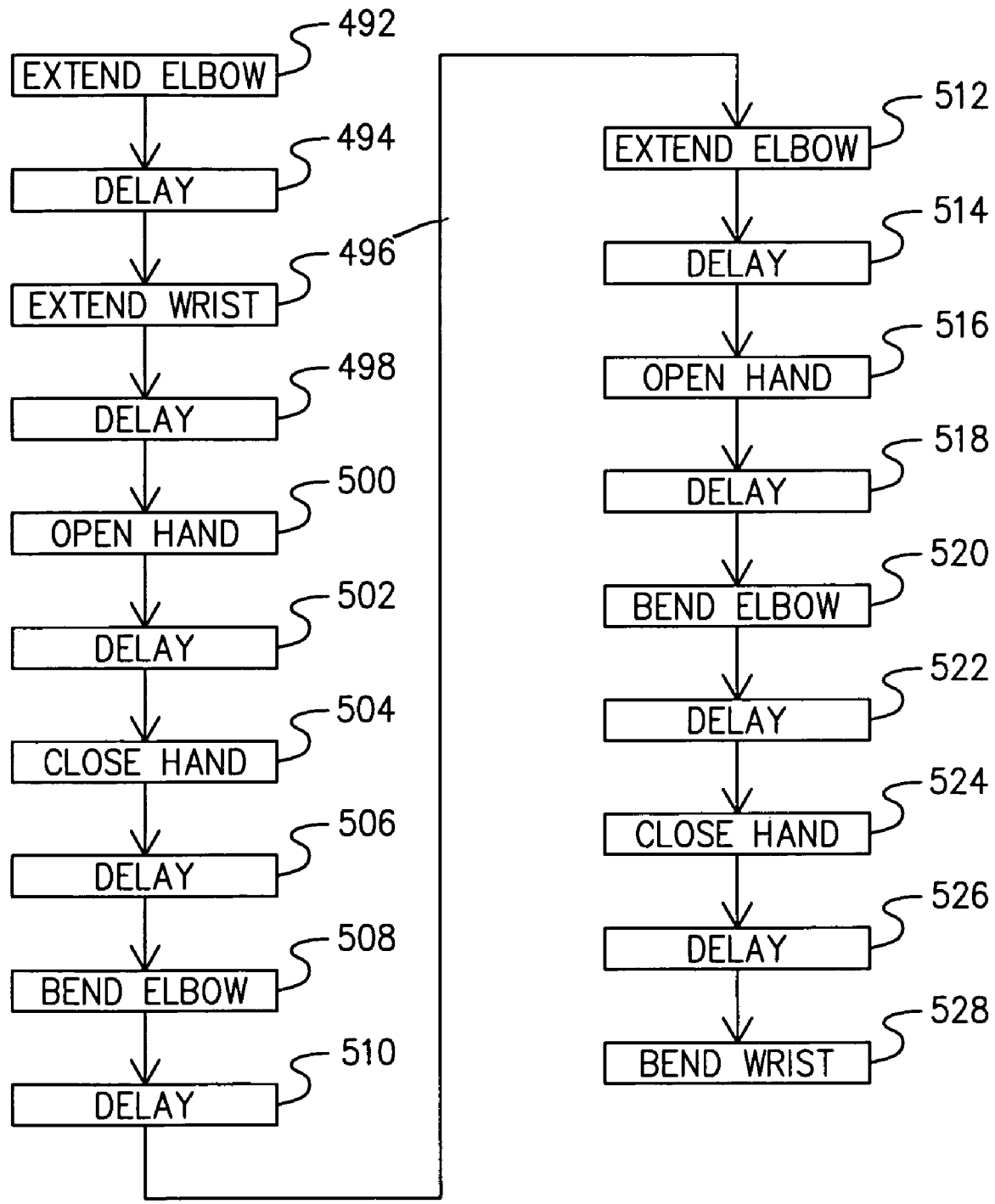

Alternatively, a functional result can be achieved, i.e., a result that directly restores use of a portion of the patient's body that otherwise suffers a neurological deficit. For example, the timing diagram 490 of FIG. 15A and its associated flow chart comprised of blocks 492-528 (see FIG. 15B) and associated timing marks 492'-516' (see FIG. 15A) that stimulate muscles via associated implantable devices 100 in three sets, a first set for the elbow extensors, a second set for the wrist extensors and a third set for the finger and thumb extensors. The activation of the associated sets of implantable devices and the timing between activations (or causing concurrent activations) is determined according to a program within the system controller 402 which is preferably user selectable, e.g., via a switch 406 on the system controller 402. Preferably, this sequence and associated timing may be determined/altered via the fitting system 450 shown in FIG. 13. Preferably, this sequence is additionally dependent upon various sensors (previously described). Accordingly, following a switch 406 activation (or sensing of a predetermined neurological sequence), the process begins with block 492. Inputs from the previously described goniometer (either internally located within a plurality of implantable devices 100 or externally located as shown as goniometer 408 in FIG. 8) or a delay in block 494 then triggers block 496 and consequently begins extension of the patient's wrist and, following a predetermined delay in block 498, begins opening of the patient's hand at block 500. Upon detection of the target location, e.g., container 404, or a delay in block 502 the patient's hand is commanded to close (or actually, the stimulation signal that causes it to open may be removed) at block 504. Following a time delay in block 506 (or switch activation or sensing of a predetermined neurological sequence), the patient's elbow now begins to bend at block 508 (again, in this case, this may be done by removing the signal that causes the patient's elbow to extend) to now take the retrieved container 404 back towards the patient during a delay in block 510. Following activation of switch 406 (or sensing of a predetermined neurological signal), the reverse sequence begins at block 512 and the container 404 may be returned during a delay in block 514 to the pad 424. In this sequence, it is preferable that an embodiment is used in which the pad 424 actually detects the presence of the container 404, e.g., the aforementioned electrical connection, magnetic, accelerometer, or pressure sensing may be used to trigger block 516. Alternatively, the release sequence starting at block 516 may be instigated by a button depression (or sensing of a predetermined neurological sequence). At block 516, the patient's hand is opened to release the container 404. Following a delay in block 518, the patient's elbow is bent (or actually allowed to bend) at block 520. Following a delay in block 522, the patient's hand is closed (or actually allowed to close) in block 524. Following a delay in block 526, the patient's wrist is bent (or actually allowed to bend) in block 528, thus restoring the patient's arm to its rest, i.e., non-stimulated, position.

Typically, the setting of the stimulation parameters of the implantable devices, e.g., amplitude, duration, frequency, etc., are set by the medical practitioner in response to observed or measured responses from the patient. However, due to the presence of the goniometric functionality described above in reference to FIGS. 8 and 12, systems of the present invention may additionally include the capability of adjusting its stimulation parameters based upon measurements by the goniometric measuring devices, e.g., the external goniometric sensor 408 or the internal goniometers described above that are formed from two or more implantable devices 100 and their associated communications between devices. For example, it is anticipated that as systems of the present invention are used, the patient's muscle tone will improve and the required stimulation parameters may be decreased, e.g., the associated amplitude, duration, and/or frequency, etc., may be decreased while retaining the same level/speed of the associated bending rate of a muscle joint. Alternatively, a desired rate of goniometric change, i.e., bending rate of a muscle joint, could be specified and the stimulation parameters could be automatically adjusted to obtain the desired goniometric response. Finally, the rate of change of the goniometric response with a constant set of stimulation parameters or the rate of change of the automatic adjustment of the stimulation parameters to retain a desired rate of goniometric change could be used as a metric to determine how well the patient is responding to treatment. This metric, i.e., the associated data, could then be communicated to the patient control unit 174, the clinician's programmer 172, or fitting system 450 (at PC 462).

Accordingly, what has been shown is a system and method that facilitates stimulating neural pathways, e.g., muscles and/or associated nerves, of a patient's body for the purpose of medical treatment by rehabilitating weakened muscles and using neuroplasticity to retrain sequential muscle movements and/or to provide the ability to directly deliver functional motor movements. While the invention has been described by means of specific embodiments and applications thereof, it is understood that numerous modifications and variations could be made thereto by those skilled in the art without departing from the spirit and scope of the invention. For example, while proximity sensors have been described as being formed from a magnetic sensor, a metal sensor, an infrared sensor, an ultrasonic emitter/sensor, an accelerometer, a pressure sensor, or a machine vision based controller, a radar emitter/sensor may also be used to perform this function. Additionally, while the present invention is particularly suited to therapeutic treatment and or functional stimulation of upper limbs in response to a neurological deficit, e.g., following a stroke, the described functions and devices could be equally useful in treating other neurological deficits, e.g., foot drop following a stroke, multiple sclerosis, cerebral palsy, spinal cord injury, etc., and is not limited to the particular muscles or muscle groups or activations shown or described, which are only exemplary uses of the present invention. It is therefore to be understood that within the scope of the claims, the invention may be practiced otherwise than as specifically described herein.

What is claimed is:

1. A system for sequentially activating a plurality of distinct neural pathways in a patient's body, said system comprising:
  a first set of one or more discrete implantable devices suitable for placement proximate to a first neural pathway for stimulating the first neural pathway;
  a second set of one or more discrete implantable devices suitable for placement proximate to a second neural pathway for stimulating the second neural pathway;
  wherein each of said discrete implantable devices is contained within a sealed elongate housing having an axial dimension of less than 60 mm and a lateral dimension of less than 6 mm and includes at least two electrodes integral with and on opposing ends of said housing, whereby said housings are suitable for injection into the patient's body and said discrete implantable devices are configured for affecting at least one neural pathway of the patient's body via said electrodes in response to first communication/control circuitry mounted within each said housing and responsive to a unique predefined identification address for each of said discrete implantable devices;
  a system controller having second communication/control circuitry configured for wireless communication with said first communication/control circuitry within each of said discrete implantable devices;
  wherein following a first activation sequence of said first neural pathway transmitted from said system controller to said first set of one or more discrete implantable devices, said system controller additionally transmits a temporally displaced, by a predetermined delay, second activation sequence to said second set of one or more discrete implantable devices; and
  a position sensor in communication with said system controller for determining the relative position of at least two portions of the patients body; and
  wherein said temporal displacement between transmitting said first and second activation sequences to said first and second sets of one or more discrete implantable devices is determined at least in part according to information communicated from said position sensor.

2. The system of claim 1 wherein said position sensor is positioned external to the patient's body.

3. The system of claim 1 wherein at least a portion of said first and second sets of one or more discrete implantable devices is configured to wirelessly determine the relative positions of at least portions of said first and second sets of one or more discrete implantable devices and thus operate as said position sensor which is positioned internal to the patient's body.

4. The system of claim 1 wherein at least two of said discrete implantable devices are configured to be positioned at different portions of a selected muscle or muscle group and are additionally configured to wirelessly determine the relative positions of said discrete implantable devices and thereby the amount of extension or retraction of the selected muscle and accordingly movement of an associated body portion and thus said discrete implantable devices operate as said position sensor which is positioned internal to the patient's body.

5. The system of claim 1 wherein said position sensor is configured for wireless communication with said system controller.

6. The system of claim 1 wherein at least a portion of said discrete implantable devices is configured to receive power from an externally-provided AC magnetic field.

7. The system of claim 6 wherein said system controller is located external to the patient's body and said externally-provided AC magnetic field is provided from said system controller.

8. The system of claim 1 wherein at least a portion of said discrete implantable devices additionally comprise a rechargeable battery that is suitable for charging via an externally-provided AC magnetic field.

9. The system of claim 1 wherein said system controller is configured for implantation within the patient's body.

10. The system of claim 1 wherein said system controller is configured for use external to the patient's body.

11. The system of claim 1 additionally comprising:
  a third set of one or more discrete implantable devices suitable for placement proximate to a third neural pathway for stimulating the third neural pathway;
  a proximity sensor in communication with said system controller for sensing a proximity of a portion of the patient's body to a predetermined goal position; and wherein
  in response to reaching said predetermined goal position, said system controller transmits a third activation sequence to one or more discrete implantable devices in said third set of one or more discrete implantable devices.

12. The system of claim 11 wherein said proximity sensor is selected from the group consisting of a magnetic sensor, a metal sensor, an infrared sensor, an ultrasonic emitter/sensor, a radar emitter/sensor, an accelerometer, a pressure sensor, and a machine vision based controller.

13. The system of claim 11 wherein said proximity sensor is positioned proximate to the patient's hand.

14. The system of claim 11 wherein said proximity sensor is located external to the patient's body and is configured to wirelessly communicate to said system controller.

15. The system of claim 11 wherein said proximity sensor is located external to the patient's body and is configured to communicate with one or more discrete implantable devices to determine the relative distance between said externally located proximity sensor and one or more of said discrete implantable devices.

16. The system of claim 1 wherein said system controller commences said first activation sequence in response to an activation signal.

17. The system of claim 16 wherein said activation signal originates from a switch.

18. The system of claim 16 wherein said activation signal originates in response to a sensed neurological signal.

19. The system of claim 18 wherein said neurological signal is sensed by one of said discrete implantable devices.

20. A system for sequentially activating a plurality of distinct neural pathways in a patient's body, said system comprising:
- a first set of one or more discrete implantable devices suitable for placement proximate to a first neural pathway for stimulating the first neural pathway corresponding to bending of the patient's elbow;
- a second set of one or more discrete implantable devices suitable for placement proximate to a second neural pathway for stimulating the second neural pathway corresponding to bending of the patient's wrist;
- a third set of one or more discrete implantable devices suitable for placement proximate to a third neural pathway for stimulating the third neural pathway corresponding to bending of one or more of the patient's fingers;
- wherein each of said discrete implantable devices is contained within a sealed elongate housing having an axial dimension of less than 60 mm and a lateral dimension of less than 6 mm and includes at least two electrodes integral with and on opposing ends of said housing, whereby said housings are suitable for injection into the patient's body and said discrete implantable devices are configured for affecting at least one neural pathway of the patients body via said electrodes in response to first communication/control circuitry mounted within each said housing and responsive to a unique predefined identification address for each of said discrete implantable devices;
- a system controller having second communication/control circuitry configured for wireless communication with said first communication/control circuitry within each of said discrete implantable devices;
- wherein following a first activation sequence of said first neural pathway transmitted from said system controller to said first set of one or more discrete implantable devices, said system controller additionally transmits a temporally displaced, by a predetermined delay, second activation sequence to said second set of one or more discrete implantable devices and a third activation sequence to said third set of one or more discrete implantable devices; and
- a position sensor in communication with said system controller for determining the relative position of at least two portions of the patient's body; and
- wherein said temporal displacement between transmitting said first and second activation sequences to said first and second sets of one or more discrete implantable devices is determined at least in part according to information communicated from said position sensor.

21. The system of claim 20 wherein said position sensor is positioned external to the patient'body.

22. The system of claim 20 wherein at least a portion of said first and second sets of one or more discrete implantable devices is configured to wirelessly determine the relative positions of at least portions of said first and second sets of one or more discrete implantable devices and thus operate as said position sensor which is positioned internal to the patient's body.

23. The system of claim 20 wherein at least two of said discrete implantable devices are configured to be positioned at different portions of a selected muscle or muscle group and are additionally configured to wirelessly determine the relative positions of said devices and thereby the amount of extension or retraction of the selected muscle and accordingly movement of an associated body portion and thus said discrete implantable devices operate as said position sensor which is positioned internal to the patient's body.

24. The system of claim 20 wherein said position sensor is configured for wireless communication with said system controller.

25. The system of claim 20 wherein at least a portion of said discrete implantable devices is configured to receive power from an externally-provided AC magnetic field.

26. The system of claim 25 wherein said system controller is located external to the patient's body and said externally-provided AC magnetic field is provided from said system controller.

27. The system of claim 20 wherein at least a portion of said discrete implantable devices additionally comprise a rechargeable battery that is suitable for charging via an externally-provided AC magnetic field.

28. The system of claim 20 wherein said system controller is configured for implantation within the patient's body.

29. The system of claim 20 wherein said system controller is configured for use external to the patient's body.

30. The system of claim 20 additionally comprising:
- a proximity sensor in communication with said system controller for sensing a proximity of the patient's hand to a predetermined goal position; and wherein
- in response to reaching said predetermined goal position, said system controller transmits a third activation sequence to one or more discrete implantable devices in said third set of one or more discrete implantable devices.

31. The system of claim 30 wherein said proximity sensor is selected from the group consisting of a magnetic sensor, a metal sensor, an infrared sensor, an ultrasonic emitter/sensor, a radar emitter/sensor, an accelerometer, a pressure sensor, and a machine vision based controller.

32. The system of claim 30 wherein said proximity sensor is positioned proximate to the patient's hand.

33. The system of claim 30 wherein said proximity sensor is located external to the patient's body and is configured to wirelessly communicate to said system controller.

34. The system of claim 30 wherein said proximity sensor is located external to the patient's body and is configured to communicate with one or more discrete implantable devices to determine the relative distance between said externally located proximity sensor and one or more of said discrete implantable devices.

35. The system of claim 20 additionally comprising:
- a proximity sensor in communication with said system controller for sensing that the patient's hand has reached a predetermined goal position; and wherein
- in response to detecting that the patient's hand has reached said predetermined goal position, said system controller transmits a third activation sequence to one or more discrete implantable devices in said third set of discrete implantable devices.

36. The system of claim 35 wherein said proximity sensor is selected from the group consisting of a magnetic sensor, a metal sensor, an infrared sensor, an ultrasonic emitter/sensor, an accelerometer, a pressure sensor, an electrical signal detector, and a machine vision based controller.

37. The system of claim 20 wherein said system controller commences said first activation sequence in response to an activation signal.

38. The system of claim 37 wherein said activation signal originates from a switch.

39. The system of claim 37 wherein said activation signal originates in response to a sensed neurological signal.

40. The system of claim 39 wherein said neurological signal is sensed by one of said discrete implantable devices.

41. A system for determining the movement of a body portion associated with a selected muscle or muscle group, said system comprising:
- a first discrete implantable device suitable for implantation in a first portion of the selected muscle or muscle group;
- a second discrete implantable device suitable for implantation in a second portion of the selected muscle or muscle group;
- wherein each of said discrete implantable devices is contained within a sealed elongate housing having an axial dimension of less than 60 mm and a lateral dimension of less than 6 mm, whereby said housings are suitable for injection into the patient's body; and
- wherein said discrete implantable devices are configured to wirelessly communicate signals to determine their relative distance and accordingly the relative extension or retraction of the selected muscle or muscle group and accordingly movement of the associated body portion.

42. The system of claim 41 wherein said discrete implantable devices additionally include at least two electrodes integral with and on opposing ends of said housing and are configured for affecting at least one neural pathway of the patient's body via said electrodes in response to signals received by first communication/control circuitry mounted within each said housing and responsive to a unique predefined identification address for each of said discrete implantable devices.

43. The system of claim 41 additionally comprising a system controller having second communication control circuitry configured for wireless communication with said first communication/control circuitry within each of said discrete implantable devices to send command signals to each of said discrete implantable devices; and wherein
- said system controller is configured to modify command signals to said discrete implantable devices that cause stimulation of neural pathways within the patient's body in response to relative distance signals measured by said discrete implantable devices.

* * * * *